US010802019B2

(12) United States Patent
Vincent et al.

(10) Patent No.: US 10,802,019 B2
(45) Date of Patent: Oct. 13, 2020

(54) METHOD FOR DETECTING GABAA RECEPTOR AUTOANTIBODIES

(71) Applicant: Oxford University Innovation Limited, Oxford (GB)

(72) Inventors: Angela Vincent, Oxford (GB); Philippa Pettingill, Oxford (GB); Patrick Waters, Oxford (GB)

(73) Assignee: Oxford University Innovation Limited, Oxford (GB)

( * ) Notice: Subject to any disclaimer, the term of this patent is extended or adjusted under 35 U.S.C. 154(b) by 0 days.

(21) Appl. No.: 15/313,025

(22) PCT Filed: May 12, 2015

(86) PCT No.: PCT/GB2015/051388
§ 371 (c)(1),
(2) Date: Nov. 21, 2016

(87) PCT Pub. No.: WO2015/177512
PCT Pub. Date: Nov. 26, 2015

(65) Prior Publication Data
US 2017/0153234 A1 Jun. 1, 2017

(30) Foreign Application Priority Data
May 23, 2014 (GB) .................................. 1409234.0

(51) Int. Cl.
| | |
|---|---|
| *G01N 33/564* | (2006.01) |
| *A61K 31/56* | (2006.01) |
| *A61K 31/664* | (2006.01) |
| *A61K 35/16* | (2015.01) |
| *A61K 38/13* | (2006.01) |
| *G01N 33/68* | (2006.01) |
| *C07K 16/28* | (2006.01) |
| *H03K 17/10* | (2006.01) |
| *C07K 16/00* | (2006.01) |
| *C07K 16/42* | (2006.01) |
| *H03K 17/16* | (2006.01) |
| *H03K 17/082* | (2006.01) |

(52) U.S. Cl.
CPC ........... *G01N 33/564* (2013.01); *A61K 31/56* (2013.01); *A61K 31/664* (2013.01); *A61K 35/16* (2013.01); *A61K 38/13* (2013.01); *C07K 16/00* (2013.01); *C07K 16/286* (2013.01); *C07K 16/4258* (2013.01); *G01N 33/6896* (2013.01); *H03K 17/107* (2013.01); *C07K 2317/21* (2013.01); *C07K 2317/33* (2013.01); *C07K 2317/76* (2013.01); *G01N 2333/70571* (2013.01); *G01N 2800/2835* (2013.01); *G01N 2800/2857* (2013.01); *G01N 2800/2871* (2013.01); *G01N 2800/30* (2013.01); *G01N 2800/301* (2013.01); *G01N 2800/50* (2013.01); *H03K 17/0828* (2013.01); *H03K 17/168* (2013.01)

(58) Field of Classification Search
CPC ............. G01N 33/564; G01N 33/6896; G01N 2800/2871; G01N 2800/2835; G01N 2800/30; G01N 2800/301; G01N 2333/70571; C07K 2317/33; C07K 16/18; C07K 16/286
See application file for complete search history.

(56) References Cited

U.S. PATENT DOCUMENTS

2015/0018251 A1* 1/2015 Lesage ............... G01N 33/6845
506/18
2016/0326227 A1* 11/2016 Dalmau ............... G01N 33/564

FOREIGN PATENT DOCUMENTS

| EP | 1292676 B1 | 7/2009 | |
|---|---|---|---|
| WO | 2011/041433 A1 | 4/2011 | |
| WO | 2014/202978 A1 | 12/2014 | |
| WO | 2015/055776 A1 | 4/2015 | |
| WO | WO-2015055776 A1 * | 4/2015 | ........... G01N 33/564 |

OTHER PUBLICATIONS

Wikipedia entry for Autoimmune encephalitis, retrieved on Mar. 5, 2018, 24 pages. (Year: 2018).*
McDaneld LM et al. Immunomodulatory therapies in neurologic critical care. Neurocrit. Care, 12: 132-143. (Year: 2010).*
Raju R et al. Autoimmunity to GABAA-receptor-associated protein in stiff-person syndrome. Brain, 129:3270-3276. (Year: 2006).*
Benarroch EE. GABAA receptor heterogeneity, function, and implications for epilepsy. Neurology, 2007, 68, 612-614. (Year: 2007).*
Ohkawa et al. "Identification of Characterization of GABAA Receptor Autoantibodies in Autoimmune Encephalitis" Journal of Neuroscience, (2014), 34, 8151-8163.
Petit-Pedrol et al., "Encephalitis with refractory seizures, status epilepticus, and antibodies to the GABAA receptor: a case series, characterisation of the antigen, and analysis of the effects of antibodies" Lancet Neurology, (2014), 13, 276-286.
Khan et al. "Antibodies to the Human y2 Subunit of the y-Aminobutyric Acid A/Benzodiazepine Receptor" Journal of Neurochemistry, (1993), 60, 961-971.
Joshi et al. "A Mouse Monoclonal Antibody Against the y2 Subunit of GABAA Receptors" Hybridoma, (2011), 30, 537-542.
Loup et al. "Selective Alternations in GABAA Receptor Subtypes in Human Temporal Lobe Epilepsy" Journal of Neuroscience, (2000), 20, 5401-5419.
Chang et al. "Immunization against GAD Induces Antibody Binding to GAD-Independent Antigens and Brainstem GABAergic Neuronal Lose" PLOS ONE, (2013), 8, e72921.
Pettingill et al. "Antibodies to Gabaa receptor a1 and y2 subunits" Neurology, (2015), 84, 1233-1241.
Akbarian et al. "GABAA Receptor Subunit Gene Expression in Human Prefrontal Cortex: Comparison of Schizophrenics and Controls" Cerebral Cortex, (1995), 5(6), 550-60.

(Continued)

Primary Examiner — Kimberly Ballard
(74) Attorney, Agent, or Firm — Norton Rose Fulbright US LLP

(57) ABSTRACT

The invention relates to methods of determining whether or not an individual has or is likely to develop a neurological disease and related methods and kits.

10 Claims, 11 Drawing Sheets
Specification includes a Sequence Listing.

(56) References Cited

OTHER PUBLICATIONS

Brenner et al. "Prevalence of neurologic autoantibodies in cohorts of patients with new and established epilepsy" Epilepsia, (2013), 54(6), 1028-35.
Dalmau et al. "Paraneoplastic Anti-N-methyl-D-aspartate Receptor Encephalitis Associated with Ovarian Teratoma" Annals of Neurology, (2007), 61(1) 25-36.
Dalmau et al. "Anti-NMDA-receptor encephalitis: case series and analysis of the effects of antibodies" The Lancet Neurology, (2008), 7(12), 1091-1098.
Hevers & Lüddens "The Diversity of GABAA Receptors—Pharmacological and Electrophysiological Properties of GABAA Channel Subtypes" Molecular neurobiology, (1998), 18(1), 35-86.
Hughes et al. "Cellular and Synaptic Mechanisms of Anti-NMDA Receptor Encephalitis" Journal of Neuroscience, (2010), 30(17), 5866-5875.
Irani et al. "N-methyl-D-aspartate antibody encephalitis: temporal progression of clinical and paraclinical observations in a predominantly non-paraneoplastic disorder of both sexes" Brain, (2010), 133(6), 1655-1667.
Irani et al. "Antibodies to Kv1 potassium channel-complex proteins leucine-rich, glioma inactivated 1 protein and contactin-associated protein-2 in limbic encephalitis, Morvan's syndrome and acquired neuromyotonia" Brain, (2010), 133(9), 2734-48.
Irani et al. "Faciobrachial Dystonic Seizures Precede Lgi1 Antibody Limbic Encephalitis" Annals of Neurology, (2011), 69(5), 892-900.
Lai et al. "AMPA receptor antibodies in limbic encephalitis alter synaptic receptor location" Annals of Neurology, (2009), 65(4), 424-434.
Lancaster et al. "Antibodies to the GABAB receptor in limbic encephalitis with seizures: case series and characterisation of the antigen" The Lancet Neurology, (2010), 9(1), 67-76.
Limon et al. "Loss of functional GABAA receptors in the Alzheimer diseased brain" PNAS, (2012), 109(25), 10071-6.
MacDonald et al. "Mutations in GABAA receptor subunits associated with genetic epilepsies" The Journal of Physiology, (2010), 588(11), 1861-1869.
McKernan & Whiting "Which GABAA,-receptor subtypes really occur in the brain?" Trends in Neurosciences, (1996), 19(4), 139-43.
Prüss et al. "N-Methyl-D-Aspartate Receptor Antibodies in Herpes Simplex Encephalitis" Neurology, (2012), 78(22), 1743-53.
Prüss et al. "IgA NMDA receptor antibodies are markers of synaptic immunity in slow cognitive impairment" Annals at neurology, (2012), 72(6), 902-11.
Rose & Bona "Defining criteria for autoimmune diseases (Witebsky postulates revisited)" Immunology today, (1993), 14(9), 426.
Steiner et al. "Increased Prevalence of Diverse N-Methyl-D-Aspartate Glutamate Receptor Antibodies in Patients With an Initial Diagnosis of Schizophrenia" JAMA psychiatry, (2013), 70(3), 271-8.
Tiihonen et al. "Cerebral benzodiazepine receptor binding and distribution in generalized anxiety disorder: a fractal analysis" Molecular Psychiatry, (1997), 2(6), 463-71.
Titulaer et al. "Treatment and prognostic factors for long-term outcome in patients with anti-N-Methyl-D-Aspartate (NMDA) receptor encephalitis: a cohort study" Lancet neurology, (2013), 12(2),157-65.
Tretter et al. "Stoichiometry and Assembly of a Recombinant GABAA Receptor Subtype" The Journal of neuroscience, (1997), 17(8), 2728-37.
Tsutsui et al."Anti-NMDA-receptor antibody detected in encephalitis, schizophrenia, and narcolepsy with psychotic features" BMC Psychiatry, (2012), 12, 37.
Tüzüñet al. "Evidence for antibody-mediated pathogenesis in anti-NMDAR encephalitis associated with ovarian teratoma" Acta neuropathologica, (2009), 118(6), 737-43.
Vincent et al. "Potassium channel antibody-associated encephalopathy: a potentially immunotherapyresponsive form of limbic encephalitis" Brain (2004), 127(3), 701-12.
Iorio, Raddaele; et al; "Astrocytic Autoantibody of Neuromyelitis Optica (NMO-IgG) Binds to Aquaporin-4 Extracellular Loops, Monomers, Tetramers and High Order Arrays"; National Institutes of Health, J. Autoimmun. Feb. 2013; 40: 21-27.
P.J. Waters, et al; "Serologic Diagnosis of NMO—A Multicenter Comparison of Aquaporin-4-IgG Assays"; Neurology 2012;78;665-671 Published Online before print Feb. 1, 2012.
Gao et at."GABAA-receptor subunit composition in the circadian timing system", Brain Research, (1995), 700, 142-156.
Marianna Spatola, et al; "Investigations in GABAA Receptor Antbody-Associated Encephalitis" American Academy of Neurology; 2017, Neurology;88:1012-1020.

* cited by examiner

Fig. 2A

Index patient
α1-specific
antibodies

Patient #11
γ2-specific
antibodies

Patient #9
Undefined
subunit
specificity

Fig. 2D aa 44-63: ILDRLLDGTDNRLRPGLGER
aa 105-119: GRMTVLRLNNLMASK
aa 204-213: SVVVAEDGSR
aa 281-300: TVFGVTTVLMTLSISA
aa 247-263: SVVPEKPEKVKDFLNK
aa 395-451: EKQLKAVTRRQ

Fig. 4A

METHOD FOR DETECTING GABAA RECEPTOR AUTOANTIBODIES

CROSS REFERENCE TO RELATED APPLICATIONS

This application is a national phase application under 35 U.S.C. § 371 that claims priority to International Application No. PCT/GB2015/051388 filed May 12, 2015, which claims priority to Great Britain Patent Application No. 1409234.0 filed May 23, 2014, all of which are incorporated herein by reference in their entirety.

FIELD OF THE INVENTION

The invention relates to methods of determining whether or not an individual has or is likely to develop a neurological disease and related methods and kits.

BACKGROUND OF THE INVENTION

In recent years, antibodies directed against proteins expressed in the central nervous system (CNS) have been identified in a number of neurological disorders. These conditions include various forms of encephalopathy (Dalmau et. al. 2007, Lai et. al. 2009, Lancaster et. al. 2010) as well as subgroups of patients with epilepsy (Irani et. al. 2011, Brenner et al. 20130 or psychiatric features (Steiner et. al. 2013, Tsutsui et. al. 2012). The antibodies are directed against extracellular epitopes of proteins expressed on the cell surface of neuronal cells, including NMDA receptors (NMDAR), voltage-gated potassium channel (VGKC)-complex antigens LGI1, contactin associated protein-like 2 (CASPR2) or glycine receptors (Dalmau et al. 2014). The discoveries of these antibodies in patient sera and cerebrospinal fluid (CSF) have altered disease management, and many of the patients have a favourable response to immunotherapies (Vincent et. al. 2004, Irani et. al. 2010; Dalmau et. al. 2008, Titulaer et. al. 2013).

Antibodies to the $GABA_A$ receptor ($GABA_AR$), a heteropentameric ligand gated ion channel that mediates the majority of inhibitory neurotransmission in the brain, have recently been reported (Petit-Pedrol et. al. 2014). The antibodies were against the $\alpha 1$ and $\beta 3$ subunits of the receptor and the patients fell into two groups with high or low $GABA_AR$-antibody titres. The six patients with high serum and CSF $GABA_AR$-antibodies ($GABA_AR$-Abs) developed a severe form of encephalitis associated with seizures or refractory status epilepticus, whereas lower serum titre antibodies were observed in 12 neurological disease controls where the clinical significance was less clear.

SUMMARY OF THE INVENTION

The inventors have unexpectedly identified the $\gamma$ subunit of the $GABA_A$ receptor as a novel target in CNS-autoimmunity. Autoantibodies against the $\gamma$ subunit of the $GABA_A$ receptor may therefore be used to diagnose or prognose neurological diseases. Accordingly, the invention provides a method of determining whether or not an individual has or is likely to develop a neurological disease, the method comprising detecting the presence or absence of one or more autoantibodies against the $\gamma$ subunit of the $\gamma$-aminobutyric acid A receptor ($GABA_AR$) in the individual, wherein the presence of one or more autoantibodies indicates that the individual has or is likely to develop the disease and wherein the absence of any autoantibodies indicates that the individual does not have or is not likely to develop the disease.

The invention also provides:

a method of treating or preventing a neurological disease in an individual who has been determined as having the disease or as likely to develop the disease using a method as defined above, the method comprising administering a therapeutically or prophylactically effective amount of a suitable therapy to the individual and thereby treating or preventing the disease;

a method of treating or preventing a neurological disease in an individual, the method comprising (i) determining whether or not the individual has or is likely to develop the disease using a method as defined above, and (ii), if the individual has or is likely to develop the disease, administering a therapeutically or prophylactically effective amount of a suitable therapy to the individual and thereby treating or preventing the disease;

a method of determining whether or not a neurological disease in an individual has an autoimmune component, the method comprising detecting the presence or absence of one or more autoantibodies in the individual using a method as defined above, wherein the presence of one or more autoantibodies indicates the disease has an autoimmune component and wherein the absence of any autoantibodies indicates the disease does not have an autoimmune component;

a method of treating a neurological disease in an individual wherein the disease has been determined as having an autoimmune component using a method as defined above, the method comprising administering a therapeutically or prophylactically effective amount of an immunotherapy to the individual and thereby treating or preventing the disease;

a method of treating a neurological disease in an individual, the method comprising (i) determining whether or not the disease has an autoimmune component using a method as defined above, and (ii), if the neurological disease has an autoimmune component, administering a therapeutically or prophylactically effective amount of an immunotherapy to the individual and thereby treating or preventing the disease;

an isolated autoantibody against the $\gamma$ subunit of the $\gamma$-aminobutyric acid A receptor ($GABA_AR$);

an immunoassay plate comprising an autoantibody as defined above;

a secondary antibody which is capable of binding to the autoantibody as defined above for use in a method of determining whether or not an individual has or is likely to develop a neurological disease; and a kit for detecting in an individual the presence or absence one or more autoantibodies against the $\gamma$ subunit of the $\gamma$-aminobutyric acid A receptor ($GABA_AR$), the kit comprising (i) the $\gamma$ subunit of the $\gamma$-aminobutyric acid A receptor ($GABA_AR$) and (ii) a secondary antibody which is capable of binding to the autoantibody as defined above.

BRIEF DESCRIPTION OF THE FIGURES

FIG. 4A shows rat peptide sequences (SEQ ID NO:4, SEQ ID NO:5, SEQ ID NO:6, SEQ ID NO:7, SEQ ID NO:8, and SEQ ID NO:9) identified that correspond to the α1 subunit of the GABA$_A$ receptor.

BRIEF DESCRIPTION OF THE SEQUENCES

Figure 1A:
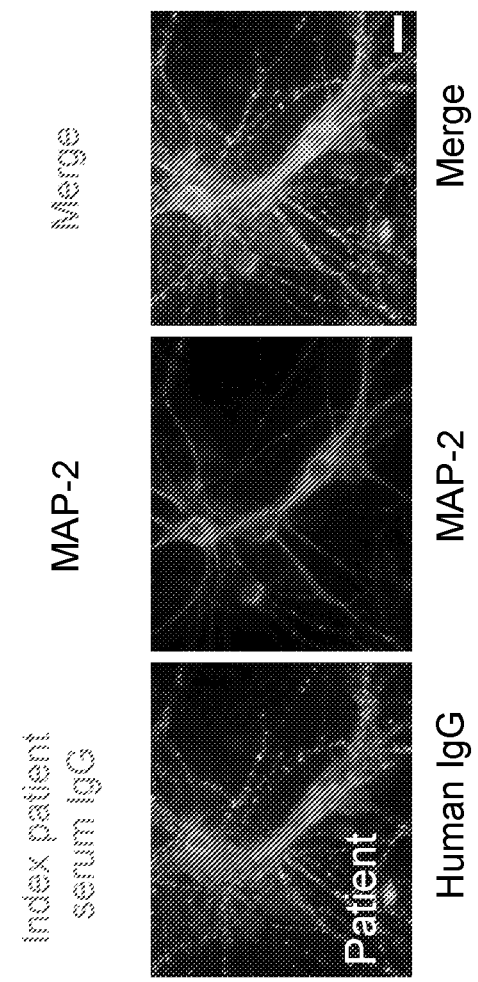
FIG. 1 shows identification of the $GABA_A$ receptor as an antibody target in CNS disease. A. The index patient sera showed intense IgG binding (green) to the surface of live hippocampal neurons identified post-permeabilisation with neuronal marker MAP2 (red). B. After identification of $GABA_A$ receptor peptides in the immunoprecipitate, the presence of $GABA_A$ receptor (52 kDa) was confirmed by western blotting using commercial antibody against the α1 subunit; cortical brain homogenate (Cx) was used as positive control. C. A cell based assay (CBA) was developed using HEK293 co-transfected the α1, β2 and γ2 subunits of the GABA$_A$ receptor. IgG antibodies binding GABA$_A$R was demonstrated with serum from Case 1 (red) which co-localised with commercial antibody against the α1 subunit (green). IgG immunoreactivity to the GABA$_A$ receptor was not observed in control serum. D. GABA$_A$R antibodies were detected in 45 patients by CBAs with α1β2γ2 subunits (FIG. 1D) and not in 92 healthy control sera. Scale bars represent 50 μm.

SEQ ID NO: 1 shows the amino acid of the human GABA$_A$R subunit γ2.
SEQ ID NO: 2 shows the amino acid of the human GABA$_A$R subunit α1.
SEQ ID NO: 3 shows the amino acid sequence of the human GABA$_A$R subunit β2.
SEQ ID NOs:4 to 9 show the amino acid sequences of the rat GABA$_A$R subunit α1 as set forth in FIG. 4A.

DETAILED DESCRIPTION OF THE INVENTION

It is to be understood that different applications of the disclosed products and methods may be tailored to the specific needs in the art. It is also to be understood that the terminology used herein is for the purpose of describing particular embodiments of the invention only, and is not intended to be limiting.

In addition as used in this specification and the appended claims, the singular forms "a", "an", and "the" include plural referents unless the content clearly dictates otherwise. Thus, for example, reference to "an autoantibody" includes two or more such autoantibodies, reference to "a disease" includes two or more such diseases, and the like.

All publications, patents and patent applications cited herein, whether supra or infra, are hereby incorporated by reference in their entirety.

Methods of Detecting Autoantibodies

The present invention relates to a method of determining whether or not an individual has or is likely to develop a neurological disease. The method of the invention comprises detecting the presence or absence of one or more autoantibodies against the γ subunit of the γ-aminobutyric acid A receptor (GABA$_A$R) in a sample from the individual.

There are two classes of GABA receptor, GABA$_A$ (which are ionotropic cell surface receptors) and GABA$_B$ (which are G-protein coupled receptors). GABA$_A$ receptors predominantly mediate the fast-inhibitory neurotransmission in the brain. On activation, influx of chloride ions results in hyperpolarisation and stabilisation of the neuronal membrane potential. The GABA$_A$Rs are the therapeutic target of many clinically important drugs, such as barbiturates, benzodiazepines and phenytoin, with anticonvulsants, anxiolytics, sedative, cognitive and mood altering properties (Woods 1992).

The GABA$_A$ receptors are usually assembled as heteropentamers. The five subunits of the GABA$_A$ receptor may originate from eight gene families that encode different isoforms (α1-6, β1-3, γ1-3, δ, ϵ, θ, π, and ρ1-3). Typically, the GABA$_A$ receptor comprises (i) α1, β2 and γ2 subunits. However, the GABA$_A$ receptor may also comprise (ii) α2, β2 and γ2 subunits, (iii) α3, β2 and γ2 subunits, (iv) α5, β2 and γ2 subunits, (v) α1, β3 and γ2 subunits, (vi) α3, β3 and γ2 subunits, or (vii) other combinations. In vivo, the GABA$_A$ receptor typically consists of 2 α1, 2 β2 and 1 γ2 subunits. The amino acid sequences of the γ2, α1 and β2 subunits of the human GABA$_A$ receptor are set forth in SEQ ID NOs:1 to 3 respectively.

In the method of the invention, the GABA$_A$ receptor comprises the γ subunit. Preferably, the GABA$_A$ receptor comprises the γ2 subunit. In the method of the invention, the GABA$_A$ receptor may further comprise the α1 and β2 subunits. Preferably, the GABA$_A$ receptor comprises 2 α1, 2 β2 and 1 γ2 subunits. in other words, the autoantibodies in the method of the invention are preferably against the GABA$_A$ receptor in it's in vivo form.

Antibodies are usually made to neutralise pathogens by binding to foreign antigens on, for example, viruses or bacteria. Autoantibodies are antibodies that individuals themselves generate against their own antigens (i.e. self antigens) and can cause disease. For example, autoantibodies may be associated with neurological diseases such as those listed below.

The invention is related to the unexpected finding that autoantibodies against the γ subunit of the GABA$_A$R may be found in patients with neurological disease more frequently than in healthy individuals. Such autoantibodies may therefore be used to diagnose a neurological disease in an individual, and the treatment of such a disease may comprise reducing the autoantibodies in the individual.

The autoantibodies described herein may also be biomarkers of a neurological disease. Disease biomarkers are typically "self" antigens. Disease biomarkers are typically antigens which are expressed in diseased tissue, but are not expressed in the corresponding normal tissue. Alternatively, disease biomarkers are typically antigens which are expressed in a diseased tissue to a greater extent than in the corresponding normal tissue. If a patient generates autoantibodies against a disease biomarker, the disease has an autoimmune component in accordance with the invention. Detection of autoantibodies against disease biomarkers in accordance with the invention may therefore be used to diagnose the neurological disease in an individual. Although neurological diseases may have an autoimmune component which allows them to be detected in accordance with the invention, they may not necessarily be treated using immunotherapy. For instance, neurological diseases, such as encephalitis, schizophrenia or epilepsy, may be treated using their typical therapies, i.e., to target the symptoms of the disease. This is discussed in more detail below.

In the method of the invention, the autoantibodies are against (i.e., specifically bind to) the γ subunit of the $GABA_A$ receptor. The autoantibodies may be against the γ1 (GABRG1), γ2 (GABRG2) or γ3 (GABRG3) subunits of the $GABA_AR$. The autoantibodies may be against the γ1, γ2 and γ3 subunits. The autoantibodies may be against the γ1 and γ2 subunits. Preferably, the autoantibodies are against the γ2 subunit. In one embodiment of the invention, the autoantibodies are against the γ2 subunit and are not against (i.e., do not specifically bind to) the γ1 or γ3 subunits. In other words, the autoantibodies specifically bind to or recognise an epitope within the γ2 subunit (i.e., as set forth in SEQ ID NO:1 or a variant thereof) but do not specifically bind to or recognise an epitope falling within the γ1 or γ3 subunits.

In the method of the invention, the autoantibody "specifically binds" to a polypeptide when it binds with preferential or high affinity to the protein for which it is specific but does substantially bind, not bind or binds with only low affinity to other polypeptides. For example, the autoantibodies specifically bind to the γ subunit of the $GABA_A$ receptor (e.g., γ1, γ2 and/or γ3) but do not specifically bind to other subunits of the $GABA_A$ receptor (e.g., α1-6, β1-3, γ1-3, δ, $\epsilon$, θ, π, and ρ1-3). In particular, the autoantibodies of the invention do not specifically bind to the α1 or β2 subunits of the $GABA_A$ receptor.

An antibody binds with preferential or high affinity if it binds with a Kd of $1 \times 10^{-6}$ M or less, more preferably $1 \times 10^{-7}$ M or less, $5 \times 10^{-8}$ M or less, more preferably $1 \times 10^{-8}$ M or less or more preferably $5 \times 10^{-9}$ M or less. An antibody binds with low affinity if it binds with a Kd of $1 \times 10^{-6}$ M or more, more preferably $1 \times 10^{-5}$ M or more, more preferably $1 \times 10^{-4}$ M or more, more preferably $1 \times 10^{-3}$ M or more, even more preferably $1 \times 10^{-5}$ M or more. A variety of protocols for competitive binding or immunoradiometric assays to determine the specific binding capability of an antibody are well known in the art (see for example Maddox et al, J. Exp. Med. 158, 1211-1226, 1993). Such immunoassays typically involve the formation of complexes between the specific protein and its antibody and the measurement of complex formation.

For the purposes of this invention, the term "autoantibody", unless specified to the contrary, includes fragments against the γ subunit of the $GABA_A$. Such fragments include Fv, F(ab') and F(ab')$_2$ fragments, as well as single chain antibodies. Typically, the autoantibodies are IgG. More typically, the autoantibodies are IgG1 or IgG3.

Any number of one or more autoantibodies against the γ subunit of the $GABA_A$ receptor may be detected in accordance with the invention, such as 2, 3, 4, 5 or more autoantibodies.

The method of the invention is carried out on any individual. The individual is typically one who is suspected of having or is likely to develop a neurological disease or for whom treatment of a neurological disease is being considered. For example, an individual who is suspected of having a neurological disease may exhibit symptoms of the disease. In other words, the individual may be symptomatic. An individual who is likely to develop a neurological disease may be genetically predisposed to produce autoantibodies or genetically predisposed to develop a neurological disease with an autoimmune component. However, such an individual may not necessarily exhibit any symptoms of the condition or disease. In other words, the individual may be asymptomatic.

Typically, the individual is human, but alternatively it may be another mammal such as a commercially farmed animal, such as a horse, a cow, a sheep or a pig, or may alternatively be a pet, such as a cat, a dog or a rodent (especially a rat or a mouse), or an experimental animal. The individual is typically a patient.

The method of the invention is typically carried out on a sample obtained from the individual. The sample may be from any tissue or bodily fluid. The sample typically comprises a body fluid and/or cells of the individual and may, for example, be obtained using a needle. The sample may be, or be derived from, plasma, serum, whole blood, urine, saliva, sweat, mucus, tears, lymph, cerebrospinal fluid (CSF), amniotic fluid, milk, faeces or nipple aspirate. Preferably the sample comprises plasma, serum, whole blood or CSF from the individual.

The sample is typically processed prior to being assayed, for example by centrifugation or by passage through a membrane that filters out unwanted molecules or cells, such as red blood cells. The sample may be measured immediately upon being taken. The sample may also be typically stored prior to assay, preferably below −70° C.

The method of the invention involves detecting the presence or absence of one or more autoantibodies against the γ subunit of the $GABA_AR$. In other words, the method involves determining whether or not the one or more autoantibodies are present in the individual or a sample from the individual. The invention may concern detecting the presence or absence of one autoantibody against the γ subunit of the $GABA_A$ receptor. In other words, the invention may concern a uniplex autoantibody assay. The invention may also concern detecting two or more autoantibodies against the γ subunit of the $GABA_A$ receptor. The invention may alternatively concern detecting the presence of autoantibodies against other antigens, i.e. two or more different autoantibodies. In other words, the invention may concern a multiplex autoantibody assay. In the multiplex assay, each autoantibody may be directed against the same antigen (e.g. the γ subunit of the $GABA_A$ receptor) or may be directed against a different antigen (e.g. the α1 and/or β2 subunits of the $GABA_A$ receptor). The autoantibody against a different antigen may be one which is also diagnostic or prognostic of neurological disease or may be diagnostic or prognostic of other diseases. In the multiplex assay, each autoantibody may be directed against more than one antigen.

The uniplex method may give a positive result, i.e. where the autoantibody is present in the sample. The uniplex method may alternatively give a negative result, i.e. where the autoantibody is not present in the sample. The multiplex method may give only positive results, i.e. all of the autoantibodies are present, or only negative results, i.e. none of the autoantibodies are present. More likely, the multiplex method may give both positive and negative results, i.e. one or more autoantibodies are present and one or more autoantibodies are absent. If an autoantibody is present, it may also be possible to quantify the autoantibody as discussed in more detail below.

The uniplex method typically comprises contacting a sample from the individual with a preparation comprising the γ subunit of the $GABA_AR$ (e.g., γ2) and detecting whether or not an autoantibody in the sample binds to the γ subunit of the $GABA_AR$ (e.g., γ2), thereby detecting the presence or absence of the autoantibody.

The multiplex method typically comprises contacting a sample from the individual with the γ subunit of the $GABA_AR$ (e.g., γ2) and optionally at least one additional (or different) antigen and detecting whether or not two or more autoantibodies in the sample bind to the γ subunit of the $GABA_AR$ (e.g., γ2) and optionally the at least one additional (different) antigen, thereby detecting the presence or absence of the two or more autoantibodies. The method preferably comprises detecting whether or not an autoantibody in the sample binds to the $GABA_AR$ (e.g., γ2) and each other antigen. An autoantibody binds to an antigen if it binds to the antigen under the conditions of the test and can be detected. The autoantibody may bind to the antigen to any degree. Methods for measuring binding are discussed below.

The method preferably comprises detecting whether or not an autoantibody in the sample specifically binds to the $GABA_AR$ (e.g., γ2). Specific binding is discussed above.

Any method may be used to detect binding or specific binding. Methods of quantitatively measuring the binding of an antibody to an antigen are well known in the art. For example, when an autoantibody specific to the antigen is present in the sample, it may bind or substantially bind with the antigen to form autoantibody-antigen complexes, which may then be detected or quantitatively measured. Binding of an antibody in the sample to the antigen indicates the presence of an autoantibody directed against the antigen in the sample. A lack of binding of an antibody in the sample to the antigen indicates the absence of an autoantibody directed against the antigen in the sample.

Detection of autoantibody-antigen complexes is typically carried out using a secondary antibody which recognises general features common to all antibodies in the individual. For instance, detection of human autoantibody-antigen complexes are typically carried out using a secondary anti-human immunoglobin antibody, typically anti-IgG or anti-human IgM, which recognises general features common to all human IgGs or IgMs respectively. Other Ig classes (IgA, IgD, IgE) can also be detected with appropriate secondary antibodies. The secondary antibody is typically labelled with a detectable label. This facilitates identification of the autoantibody-antigen complex. Any detectable label may be used. Suitable labels include, but are not limited to, fluorescent molecules, luminescent molecules, radioisotopes, e.g. $^{125}I$, $^{35}S$, enzymes, antibodies, antigens, polynucleotides and ligands such as biotin.

For instance, the secondary antibody may be conjugated to an enzyme such as, for example, horseradish peroxidise (HRP), so that detection of an autoantibody/antigen/secondary antibody complex is achieved by addition of an enzyme substrate and subsequent colorimetric, chemiluminescent or fluorescent detection of the enzymatic reaction products, or it may be conjugated to a fluorescent or luminescent signal. Alternatively, the secondary antibody may be labelled with a reporter molecule such as a heavy metal or a radioactive tag. Preferably, the intensity of the signal from the secondary antibody is indicative of the relative amount of the antigen-autoantibody complex in the sample when compared to a positive or negative control, and using different dilutions of the samples.

The binding of antibodies to antigens may be detected by any immunological assay technique, of which many are well known in the art. Examples of suitable techniques include enzyme-linked immunosorbent assay (ELISA), radioimmunoassay, luminescence assay, competition assay, inhibition assay, sandwich assay, fluorescent microscopy, microarray or fluorescence-activated cell sorting (FACS) analysis or the like.

The method of detecting the presence or absence of one or more autoantibodies may comprise outputting, optionally on a computer, (i) an indication of whether or not the one or more autoantibodies are present or absent and/or (ii) that the one or more autoantibodies are present or absent and that this indicates whether or not the individual has a disease or is likely to develop a disease with an autoimmune component.

γ Subunit of the $GABA_A$ Receptor

In the method of the invention, the one or more autoantibodies are against the γ subunit of the $GABA_A$ receptor. The method of the invention may involve the detection of autoantibodies against the γ1, γ2 and/or γ3 subunits of the $GABA_A$ receptor. The method of the invention may involve the detection of autoantibodies against variants of the γ1, γ2 and/or γ3 subunit of the $GABA_A$ receptor. Preferably, the method of the invention involves the detection of autoantibodies against the γ2 subunit of the $GABA_A$ receptor, or variants thereof. For example, the γ2 subunit of the $GABA_A$ receptor may comprise a mutation that is associated with a neurological disease. The γ2 subunit of the human $GABA_A$ receptor may have at least 98% or at least 99%, homology to SEQ ID NO:1 based on amino acid identity over their entire sequence and which are capable of binding to an autoantibody.

The above mentioned homology is calculated on the basis of amino acid identity (sometimes referred to as "hard homology"). The UWGCG Package provides programs including GAP, BESTFIT, COMPARE, ALIGN and PILEUP that can be used to calculate homology or line up sequences (for example used on their default settings). The BLAST algorithm can also be used to compare or line up two sequences, typically on its default settings. Software for performing a BLAST comparison of two sequences is publicly available through the National Center for Biotechnology Information (http://www.ncbi.nlm.nih.gov/). This algorithm is further described below. Similar publicly available tools for the alignment and comparison of sequences may be found on the European Bioinformatics Institute website (http://www.ebi.ac.uk), for example the ALIGN and CLUSTALW programs.

A BLAST analysis is preferably used for calculating identity. Software for performing BLAST analyses is publicly available through the National Center for Biotechnology Information (http://www.ncbi.nlm.nih.gov/). This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al., supra). These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) *Proc. Natl. Acad. Sci.* USA 89: 10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) *Proc. Natl. Acad. Sci.* USA 90: 5873-5787. One measure of similarity provided by the BLAST algorithm is the smallest sum probability (P(N)), which provides an indication of the probability by which a match between two polynucleotide or amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

The homologous sequences typically differ by at least 1, 2, 5, 10, 20 or more mutations (which may be substitutions, deletions or insertions of amino acids). These mutations may be measured across any of the regions mentioned above in relation to calculating identity. The substitutions are preferably conservative substitutions. These are defined according to the following Table. Amino acids in the same block in the second column and preferably in the same line in the third column may be substituted for each other:

| | | |
|---|---|---|
| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

As discussed above, the invention may concern the multiplex detection of two or more autoantibodies, each of which is directed against a different antigen. In such embodiments, the preparation comprises the γ2 subunit of the $GABA_A$ receptor together with additional antigens. Any number of additional antigens may be present in the preparation(s), such as 2 or more 3 or more, 4 or more, 5 or more, 10 or more, 20 or more, 30 or more, 40 or more or 50 or more, 100 or more, 1000 or more, or 5000 or more, such as 10,000 or 16,000, different antigens. The preparation(s) typically comprises the same number of different antigens as the number of autoantibodies being detected. The one or more additional antigens may be selected from α1-6, β1-3, γ1, γ3, δ, ⌐, θ, π, and ρ1-3 subunits of the $GABA_A$ receptor. Preferably, the one or more additional antigens are the α1 and/or β2 subunits of the $GABA_A$ receptor. For example, the one or more additional antigens may be the human α1 or β2 subunits of the $GABA_A$ receptor as set forth in SEQ ID NOs:2 and 3, or variant thereof. The α1 or β2 subunits of the human $GABA_A$ receptor may have at least 98% or at least 99% homology to SEQ ID NO:2 or 3 based on amino acid identity over their entire sequence and which are capable of binding to an autoantibody. The one or more additional antigens may be selected from, but are not limited to in any way, the human polypeptide antigens listed below:

Antigens Currently Relevant to Diagnosis of Neurological Disease

| Antigen | NCBI Accession |
|---|---|
| aquaporin-4 (AQP4) | NP_001641.1, NP_004019.1 |
| myelin-oligodendrocyte glycoprotein (MOG) | NP_996537.3, NP_001163889.1, NP_996533.2, NP_001008230.1, NP_001008229.1, NP_996534.2, NP_002424.3, NP_996535.2, NP_996532.2 |
| acetylcholine receptor (AChR) - alpha, beta, gamma, epsilon and/or delta subunit(s) | NP_000737.1, NP_001177384.1 |
| acetylcholine receptor (AChR) - beta subunit | NP_000739.1 |
| muscle specific tyrosine kinase (MuSK) | NP_005583.1, NP_001159752.1, NP_001159753.1 |
| contactin associated protein-like 2 (CASPR2) | NP_054860.1 |
| metabotropic glutamate receptor 5 (mGluR5) | NP_001137303.1, NP_000833.1 |
| metabotropic glutamate receptor 1 (mGluR1) | NP_000829.2, NP_001107801.1 |
| N-Methyl-D-aspartate (NMDA) receptor NR1 | NP_000823.4, NP_067544.1, NP_015566.1, NP_001172019.1, NP_001172020.1 |
| N-Methyl-D-aspartate (NMDA) receptor NR2A | NP_001127879.1, NP_000824.1, NP_001127880.1 |
| N-Methyl-D-aspartate (NMDA) receptor NR2B | NP_000825.2 |
| leucine-rich glioma inactivated protein 1 (LGI1) | NP_005088.1 |
| Contactin-2 (CNTN2) | NP_005067.1 |
| glutamic acid decarboxylase 1 (GAD1) | NP_038473.2, NP_000808.2 |
| glutamic acid decarboxylase 2 (GAD2) | NP_001127838.1, NP_000809.1 |
| AMPA glutamate receptor 1 (GluA1) | NP_000818.2, NP_001107655.1, NP_001244948.1, NP_001244949.1, NP_001244950.1, NP_001244951.1, NP_001244952.1 |
| AMPA glutamate receptor 2 (GluA2) | NP_000817.2, NP_001077088.1, NP_001077089.1 |
| AMPA glutamate receptor 3 (GluA3) | NP_015564.4, NP_000819.3, NP_001243672.1 |

-continued

| Antigen | NCBI Accession |
|---|---|
| GABA type B receptor subunit 1 (GABABR1) | NP_001461.1, NP_068703.1, NP_068704.2 |
| GABA receptor type B receptor subunit 2 (GABABR2) | NP_005449.5 |
| Glycine receptor alpha 1 (GlyRA1) | NP_000162.2, NP_001139512.1 |
| Glycine receptor alpha 2 (GlyRA2) | NP_002054.1, NP_001112357.1, NP_001112358.1, NP_001165413.1 |
| Glycine receptor alpha 3 (GlyRA3) | NP_006520.2, NP_001036008.1 |
| Glycine receptor alpha 4 (GlyRA4) | NP_001019623.2, NP_001165756.1 |
| Glycine receptor beta (GlyB) | NP_000815.1, NP_001159532.1, NP_001159533.1 |
| Voltage-gated calcium channel (VGCC) | NP_000713.2, NP_954856.1, NP_954855.1, NP_000714.3, NP_001193846.1, NP_001193845.1, NP_000716.2, NP_060868.2, NP_001139270.1, NP_001005747.1, NP_000717.2, NP_001005746.1, NP_001005505.1, NP_001167522.1, NP_758952.4, NP_006021.2 |
| Receptor protein tyrosine phosphatase sigma (RPTPσ) | NP_002841.3, NP_570924.2, NP_570923.2, NP_570925.2 |

The method of the invention may include the detection of one or more of the antigens listed above. The polypeptide sequences of the antigens listed above are identified by NCBI accession numbers. For some antigens, multiple NCBI accession numbers are indicated which relate to different isoforms of the respective antigens.

Neurological Diseases

In a method of the invention, the presence of one or more autoantibodies in the individual may indicate that the individual has or is likely to develop a neurological disease. Similarly, the absence of any autoantibodies in the individual may indicate that the individual does not have or is not likely to develop a neurological disease.

The phrase "has a neurological disease" means that the individual has already developed the disease, such as one of the diseases outlined below. For example, the individual may exhibit clinical features of the disease. Clinical features of particular neurological diseases is indicated in Table 2 of the Example.

The phrase "likely to develop a neurological disease" means that the individual is at risk of or has an increased risk of developing a disease. Such an individual typically does not exhibit symptoms of the disease. Such an individual may however be monitored further for possible development of the symptoms of the disease.

The phrase "does not have a neurological disease" means that the individual has not developed a disease with an autoimmune component, such as one of the diseases outlined below. The individual typically does not exhibit symptoms of the disease.

The phrase "not likely to develop a neurological disease" typically means that the individual is not at risk of or has a decreased risk of developing a disease.

The invention provides a method of determining whether or not an individual has or is likely to develop a neurological disease, comprising detecting the presence or absence of one or more autoantibodies using the method of the invention. In other words, the method of the invention may concern the diagnosis or prognosis of a neurological disease. The method of the invention may concern determining whether or not an individual is at risk of or has an increased risk of developing a neurological disease.

The neurological disease has an autoimmune component. In other word, the neurological disease involves an autoimmune response and the production of autoantibodies. The disease may be a disease or condition resulting from the presence of the autoantibody during development, such as arthrogryposis (i.e. fixed joint contractures), autism or schizophrenia. The neurological disease is typically an autoimmune disease. Preferably, the neurological disease is a central nervous system disease such as autoimmune encephalitis, limbic encephalitis, status epilepticus, epilepsy, a movement disorder or a psychiatric disorder, such as anxiety, psychosis or catatonia. Such central nervous diseases are typically associated with seizures, amnesia, behavioural changes, hallucinations, anxiety, sleep disorders, stiffness and/or rigidity.

Methods of Treating Neurological Diseases

The present invention also provides a method of treating or preventing a neurological disease in an individual who has been determined as having the disease or as likely to develop the disease using the method of the invention, comprising administering a therapeutically or prophylactically effective amount of a suitable therapy to the individual and thereby treating or preventing the disease.

Suitable therapies for treating the symptoms of a neurological disease include immunotherapies. Suitable immunotherapies include, but are not limited to, corticosteroids, intravenous immunoglobulins, plasma exchange, immunosuppressive drugs, steroid-sparing drugs (e.g. Azathioprine, mycophenolate mofetil), cyclophosphamide, cyclosporine and therapeutic monoclonal antibodies such as Rituxan and eculizumab.

The invention also provides a method of treating or preventing a neurological disease with an autoimmune component, comprising (i) determining whether or not an individual has or is likely to develop the disease using the method described above, and, (ii) if the individual has or is likely to develop the disease, administering a therapeutically or prophylactically effective amount of an immunotherapy to the individual and thereby treating or preventing the disease.

Suitable immunotherapies may be any of those described above.

The dose of therapy to be used in accordance with the invention will depend upon the nature of the specific therapy. A suitable dose can be determined by a skilled practitioner based on his common general knowledge, taking into account, for example, the regime and dose that would be used for in vivo treatment using that therapy. For example, a suitable dose may be selected to reflect the level of a therapeutic agent that would be present in the blood circulatory system of an individual after in vivo administration.

The method may be for treating the neurological disease. In the case of treating, the individual typically has the disease, i.e. has been diagnosed as having the disease, or is suspected as having the disease, i.e. shows the symptoms of the disease. As used herein, the term "treating" includes any of following: the prevention of the disease or of one or more symptoms associated with the disease; a reduction or prevention of the development or progression of the disease or symptoms; and the reduction or elimination of an existing disease or symptoms.

The method may be for preventing the neurological disease. In the case of preventing, the individual is typically likely to develop the neurological disease or is at risk of developing the neurological disease. In this embodiment, the individual can be asymptomatic. The individual can have a genetic predisposition to the neurological disease. The individual may have one or more family members with the neurological disease. As used herein, the term "preventing" includes the prevention of the onset of the neurological disease or of one or more symptoms associated with the neurological disease.

Therapy and prevention includes, but is not limited to, preventing, alleviating, reducing, curing or at least partially arresting symptoms and/or complications resulting from or associated with the neurological disease with an autoimmune component. When provided therapeutically, the therapy is typically provided at or shortly after the onset of a symptom of the neurological disease. Such therapeutic administration is typically to prevent or ameliorate the progression of, or a symptom of the disease or to reduce the severity of such a symptom or disease. When provided prophylactically, the treatment is typically provided before the onset of a symptom of the neurological disease (as above). Such prophylactic administration is typically to prevent the onset of symptoms of the neurological disease.

Specific routes, dosages and methods of administration of immunotherapies may be routinely determined by the medical practitioner. Typically, a therapeutically effective or a prophylactically effective amount of the therapy is administered to the individual. A prophylactically effective amount is an amount which prevents the onset of one or more symptoms of the disease. A therapeutically effective amount of the therapy is an amount effective to ameliorate one or more symptoms of the neurological disease. A therapeutically effective amount of the therapy is preferably an amount effective to abolish one or more of, or preferably all of, the symptoms of the neurological disease.

The therapy may be employed alone as part of a composition, such as but not limited to a pharmaceutical composition or a vaccine composition or an immunotherapeutic composition to prevent and/or treat the neurological disease.

The therapy may be used in combination with one or more other therapies intended to treat the same individual. By a combination is meant that the therapies may be administered simultaneously, in a combined or separate form, to an individual. The therapies may be administered separately or sequentially to an individual as part of the same therapeutic regimen. For example, a therapy may be used in combination with another therapy intended to treat an inflammatory or autoimmune disease. The other therapy may be a general therapy aimed at treating or improving the condition of an individual with an inflammatory or autoimmune disease. For example, treatment with methotrexate, glucocorticoids, salicylates, nonsteroidal anti-inflammatory drugs (NSAIDs), analgesics, other DMARDs, aminosalicylates, corticosteroids, and/or immunomodulatory agents (e.g., 6-mercaptopurine and azathioprine) may be combined with a therapy. The other therapy may be a specific treatment directed at the particular disease or condition suffered by the individual, or directed at a particular symptom of such a disease or condition.

The therapy may be administered to the individual by any suitable means. The immunotherapy can be administered by enteral or parenteral routes such as via oral, buccal, anal, pulmonary, intravenous, intra-arterial, intramuscular, intraperitoneal, intraarticular, topical or other appropriate administration routes.

The formulation will depend upon factors such as the nature of the therapy and the disease to be treated. The therapy may be administered in a variety of dosage forms. It may be administered orally (e.g. as tablets, troches, lozenges, aqueous or oily suspensions, dispersible powders or granules), parenterally, subcutaneously, intravenously, intramuscularly, intrasternally, transdermally or by infusion techniques. The therapy may also be administered as a suppository. A physician will be able to determine the required route of administration for each particular individual.

Typically, the therapy is formulated for use with a pharmaceutically acceptable carrier or diluent and this may be carried out using routine methods in the pharmaceutical art. The pharmaceutical carrier or diluent may be, for example, an isotonic solution. For example, solid oral forms may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. Such pharmaceutical preparations may be manufactured in known manner, for example, by means of mixing, granulating, tabletting, sugar-coating, or film coating processes.

Liquid dispersions for oral administration may be syrups, emulsions and suspensions. The syrups may contain as carriers, for example, saccharose or saccharose with glycerine and/or mannitol and/or sorbitol.

Suspensions and emulsions may contain as carrier, for example a natural gum, agar, sodium alginate, pectin, methylcellulose, carboxymethylcellulose, or polyvinyl alcohol. The suspensions or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

Solutions for intravenous or infusions may contain as carrier, for example, sterile water or preferably they may be in the form of sterile, aqueous, isotonic saline solutions.

For suppositories, traditional binders and carriers may include, for example, polyalkylene glycols or triglycerides; such suppositories may be formed from mixtures containing the active ingredient in the range of 0.5% to 10%, preferably 1% to 2%.

Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10% to 95% of active ingredient, preferably 25% to 70%. Where the pharmaceutical composition is lyophilised, the lyophilised material may be reconstituted prior to administration, e.g. a suspension. Reconstitution is preferably effected in buffer.

Capsules, tablets and pills for oral administration to an individual may be provided with an enteric coating comprising, for example, Eudragit "S", Eudragit "L", cellulose acetate, cellulose acetate phthalate or hydroxypropylmethyl cellulose.

Pharmaceutical compositions suitable for delivery by needleless injection, for example, transdermally, may also be used.

A therapeutically or prophylactically effective amount of the compound is administered. The dose may be determined according to various parameters, especially according to the compound used; the age, weight and condition of the individual to be treated; the route of administration; and the required regimen. Again, a physician will be able to determine the required route of administration and dosage for any particular individual. A typical daily dose is from about 0.1 to 50 mg per kg, preferably from about 0.1 mg/kg to 10 mg/kg of body weight, according to the activity of the specific inhibitor, the age, weight and conditions of the individual to be treated, the type and severity of the disease and the frequency and route of administration. Preferably, daily dosage levels are from 5 mg to 2 g.

Method of Determining Whether or not a Neurological Disease has an Autoimmune Component The invention provides a method of determining whether or not a neurological disease in an individual has an autoimmune component, comprising detecting the presence or absence of one or more autoantibodies in the individual using the method of the invention, wherein the presence of one or more autoantibodies indicates the disease has or is likely to have an autoimmune component and wherein the absence of any autoantibodies indicates the disease does not have or is not likely to have an autoimmune component. As discussed above, a disease has an autoimmune component if the individual generates autoantibodies that are associated with the disease.

The neurological disease may be any neurological disease as discussed above. The individual has the disease and so is typically symptomatic.

The invention also provides a method of treating a disease in an individual wherein the disease has been determined as having an autoimmune component using the method described above, comprising administering a therapeutically or prophylactically effective amount of an immunotherapy to the individual and thereby treating or preventing the disease.

Further provided is a method of treating a neurological disease in an individual, comprising (i) determining whether or not the disease has an autoimmune component using the method described above and, (ii) if the disease has an autoimmune component, administering a therapeutically or prophylactically effective amount of an immunotherapy to the individual and thereby treating or preventing the disease.

Immunotherapies are described above.

Autoantibodies of the Invention

The invention also provides isolated autoantibodies or portions thereof against (i.e., specifically bind to) the γ subunit of the $GABA_A R$. The autoantibodies of the invention are as described above. The term "isolated" means that the autoantibody is not in (i.e., has been removed from) the individual, that the antibody has been cloned from the individual or that the antibody has been sequenced and recombinantly expressed.

The invention also provides a sample from the individual comprising an autoantibody as described above.

Preferably, the autoantibodies are against the γ2 subunit of the $GABA_A R$. For example, the autoantibodies may recognise an epitope within SEQ ID NO:1 or a variant thereof, as described above. Preferably, the $GABA_A R$ further comprises the α1 and β2 subunits. More preferably, the $GABA_A R$ comprises 2 α1, 2 β2 and γ2. In other words, preferably the autoantibodies of the invention are against the $GABA_A R$ in it's in vivo form.

The autoantibodies of the invention are preferably IgG. More preferably, the IgG is IgG1 or IgG3.

The autoantibodies of the invention may used for a variety of purposes, including as reagents in commercial antibody tests etc.

Kits

The invention provides an assay kit for detecting in an individual the presence or absence of one or more autoantibodies against the γ subunit of the $GABA_A R$. The kit comprises (i) the γ subunit of the $GABA_A R$ and (ii) a secondary antibody, which is capable of binding to the autoantibody. The γ subunit of the $GABA_A R$ may be any γ subunit of the $GABA_A R$ as described above. The secondary antibody may be any secondary antibody as described above, which is capable of binding to the one or more autoantibodies and/or a detectable label. Typically, the secondary antibody binds to IgG. The secondary antibody is preferably labelled with the detectable label. Suitable detectable labels are discussed above. Preferably, the kit comprises instructions to use the kit, preferably in the method of the invention. Preferably, the kit also comprises means for contacting the preparation of the γ subunit of the $GABA_A R$ with a sample from the individual. For example, the kit preferably comprises an immunoassay plate.

The invention is illustrated by the following Example.

EXAMPLE

1. Introduction

Antibodies against cell surface and synaptic proteins are helpful in the diagnosis of immunotherapy-responsive diseases. Using immunoprecipitation from neuronal cultures and mass spectrometry, antibodies were identified that bind to the α1-subunit of the gamma-aminobutyric acid receptor ($GABA_A R$) in a patient with high VGKC-complex antibodies. Cell based assays using HEK293 cells expressing $GABA_A R\alpha1\beta2\gamma2$ led to the identification of serum $GABA_A R$-antibodies in 40 patients out of 2153 (2%) found negative for other surface neuronal antibody tests, and 5/505 (1%) with other antibodies, but not in 92 healthy sera. Eighteen of 45 (40%) of the sera bound to either the α1 (20%) or the γ2 (20%) subunits and were of IgG1 (94%) or IgG3 (6%) subclass. The remaining 27/45 (60%) had lower antibody titres (p<0.0001), were mainly IgM (p=0.005), and the $GABA_A R$ subunit specificity was not clear. Incubation of primary hippocampal neurons with $GABA_A R$-IgG1 α1 or γ2 specific sera caused a reduction in surface $GABA_A R$ levels.

The clinical features of 15 patients with $GABA_A R$-antibodies (α1 n=6, γ2 n=5, subunit-specificity unknown n=4) included seizures (53%), memory impairment (47%) and psychiatric features including hallucinations (40%) and anxiety (27%). One patient with a possible diagnosis of catatonic schizophrenia received immunotherapy and showed a substantial clinical improvement. In addition, another patient with a paraneoplastic limbic encephalitis had been treated with immunotherapies.

The $GABA_AR$ γ2-antibodies are a new autoimmune target. IgG antibodies to the γ2 subunit of this receptor have not been reported previously, and are associated principally with seizures and amnesia.

2. Methods

Patients' Samples

Case 1 was identified as a result of screening sera for binding to live neurons in culture. When identified, and an assay established, 505 sera with other antibodies, and a further 2153 referred serum samples found negative for NMDAR or other antibody tests were tested for antibodies to $GABA_AR$. Brief questionnaires were sent to referring neurologists asking for clinical details. Case 2, whose history is briefly described, gave written consent for clinical data to be published. The research use of referred sera is approved by the Oxfordshire Research Ethics Committee A (07/Q160X/28).

Immunoprecipitation from Hippocampal Neurons

Dissociated cortical and hippocampal neurons were prepared from P0 rats and stained as described previously (Irani et. al. 2010). For immunoprecipitation studies, live cortical neurons were grown in T175 $cm^2$ flasks and incubated with patient or healthy control serum (1:100) in culture medium supplemented with 25 mM Hepes for thirty minutes at 37° C. Neurons were washed, solubilised (10 mM Tris pH 7.5, 100 mM NaCl, 1 mM EDTA, 2% digitonin containing protease inhibitors) and cell extracts centrifuged at 13,000 g for 10 minutes at 4° C. Supernatants were incubated with protein-G Sepharose overnight at 4° C. and washed the following morning in solubilisation buffer. Equal amounts of SDS sample buffer containing reducing agent was added to the Sepharose beads and bound IgG-protein complexes were eluted, collected and stored at −20° C. Samples were resolved on a Tris-glycine (3-8%) gel (Nu-PAGE, Invitrogen) and protein material excised after EZBlue staining (Sigma G1041) and cut into 1-2 $mm^3$ gel pieces. Gel lanes were cut into fractions and individual fractions were digested and analysed by liquid chromatography MS analysis using an Ultimate 3000 nano-HPLC system (Dionex, Sunnyvale, Calif., USA). Raw LC-MS/MS data were processed and Mascot compatible files were created using DataAnalysis 4.0 software (Bruker Daltonics). Database searches were performed using the Mascot algorithm (version 2.4) and the UniProt_SwissProt database with a mammalian taxonomy restriction.

After identification of peptides corresponding to the α1 subunit of the $GABA_A$ receptor (FIG. 4A), western blots of immunoprecipitate were probed with a polyclonal $GABA_AR$ antibody against the alpha 1 subunit (1:500; Antibodies Inc, clone N95/35) followed by anti-mouse Ig HRP (1:2000, Dako P0447) and visualised using ECL (Pierce, #32106).

Expression of the $GABA_AR$ in Transfected HEK Cells

All cDNA plasmids encoding human sequences of the $GABA_AR$ subunits and are detailed in Table 3. Human Embryonic Kidney (HEK) cells were cultured in Dulbecco's Modified Eagle medium (DMEM) supplemented with 10% foetal calf serum (FCS) and 1% penicillin/streptomycin/amphotericin (PSA) on coverslips in 6-well plates. HEK cells were transfected initially with 3 μg of a cDNA vector encoding a single $GABA_AR$ subunits (α1, β2, β3 or γ2) or as a combined heteropentamers (6 μg total cDNA of α1β2γ2), using known methods. Thirty-six hours after transfection, surface $GABA_AR$ expression was evaluated on live unfixed cells with commercial antibodies against the individual subunits. As $GABA_AR$-subunits were observed to express at the surface of cells only with heteropentamer transfection (FIG. 4), all studies investigating patient sera were performed on cells transfected with a combination of $GABA_AR$ subunits.

$GABA_A$ Receptor Antibody Assays

As for other antibody tests (Leite et al 2008, Waters et al 2008, Irani et al 2010) the $GABA_AR$ subunits (α1, β2, β3 or γ2) or combined heteropentamers (6 μg total cDNA of α1β2γ2) were expressed in Human Embryonic Kidney (HEK) cells and serum antibody binding detected with AlexaFluor anti-human IgG (1:750, A-21090, Invitrogen). Live $GABA_AR$-transfected cells were incubated with sera (diluted 1:20 in blocking solution, DMEM supplemented with 200 mM HEPES and 1% BSA) for one hour at room temperature. Cells were washed, fixed in 3% formaldehyde, and surface IgG binding visualised with AlexaFluor anti-human IgG (1:750, A-21090, Invitrogen). Coverslips subsequently washed and mounted with fluorescent mounting medium. All sera were scored (0, negative, 1 low positive, 2-4 positive) and co-localised with a commercial antibody against the α1 subunit of the $GABA_AR$. Endpoint dilution titres were established by determining the highest dilution at which IgG binding was no longer visible. All positive sera were also tested against different $GABA_A$ receptors (α1β2γ2, α2β2γ2, α3β2γ2, α5β2γ2, α1β3γ2, α3β3γ2, α1β2γ1,) and IgG binding determined as above. Antibody IgG subclasses were determined by use of subclass specific anti-human IgG1, IgG2, IgG3 or IgG4 primary antibodies (The Binding Site, UK), before washing, fixing and visualization with Alexa Fluor IgG anti-mouse IgG 568. IgM-specific antibodies were determined using an AlexaFluor anti-human IgM antibody. All cDNA plasmids encode human sequences of the $GABA_AR$ subunits are detailed in Table 3.

Antibody Binding to $GABA_AR$ Subunits

To study the specificity of the antibodies to a defined subunit of the $GABA_AR$, all positive sera (n=45) were screened on different $GABA_A$ receptors (α1β2γ2, α2β2γ2, α3β2γ2, α5β2γ2, α1β3γ2, α3β3γ2, α1β2γ1) and IgG binding determined as above.

Determination of Immunoglobulin Subclass

Antibody IgG subclasses were determined in patients with available sera. After application of human sera, coverslips were incubated with subclass specific anti-human IgG1, IgG2, IgG3 or IgG4 primary antibodies (The Binding Site, UK), before washing, fixing and visualization with Alexa Fluor IgG anti-mouse IgG 568 (Invitrogen, A11029). IgM-specific antibodies were determined using an AlexaFluor anti-human IgM antibody (1:750, A-21215, Invitrogen).

Effects of Patient Antibodies on $GABA_AR$ Expression In Vitro

Primary cortical neuronal cultures (DIV7) were treated with patient or healthy control serum (1:100) for 3 days. Surface proteins were isolated by labelling live cells with EZ-Link® Sulfo-NHS-SS-Biotin, lysing and purifying on a neurtravidin agarose column (Pierce, 89881). Isolated membrane proteins were eluted in SDS-PAGE buffer (Invitrogen UK) containing 50 mM DTT and equal amounts of samples were analysed by SDS-PAGE and western blot as described above and probed for the α1 and γ2 subunits of the $GABA_A$ receptor. An antibody against the transferrin receptor (Invitrogen, 13-6800) was used as a loading control for surface fractions.

3. Results

Identification of the GABA$_A$R as a Target of Autoimmunity

Figure 1B:
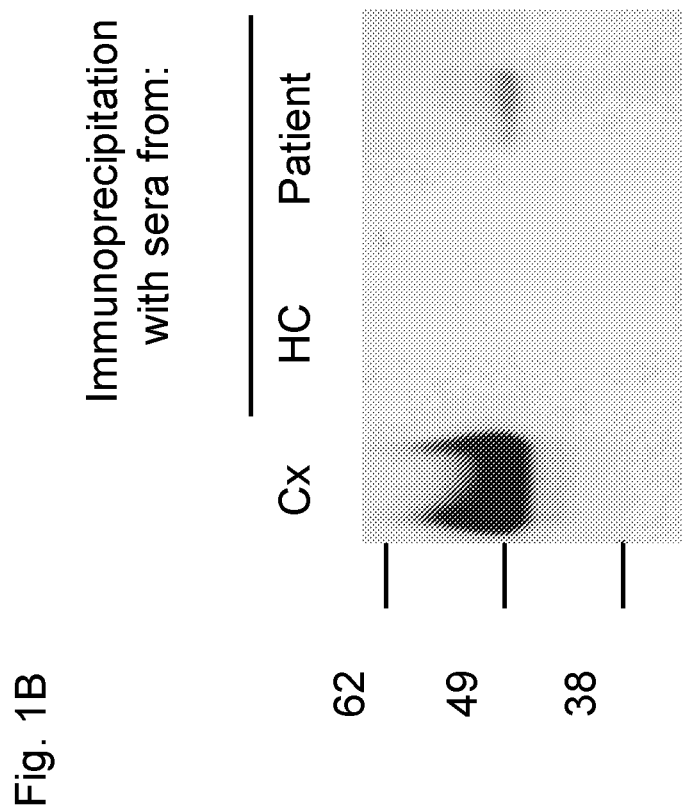
Figure 4B:
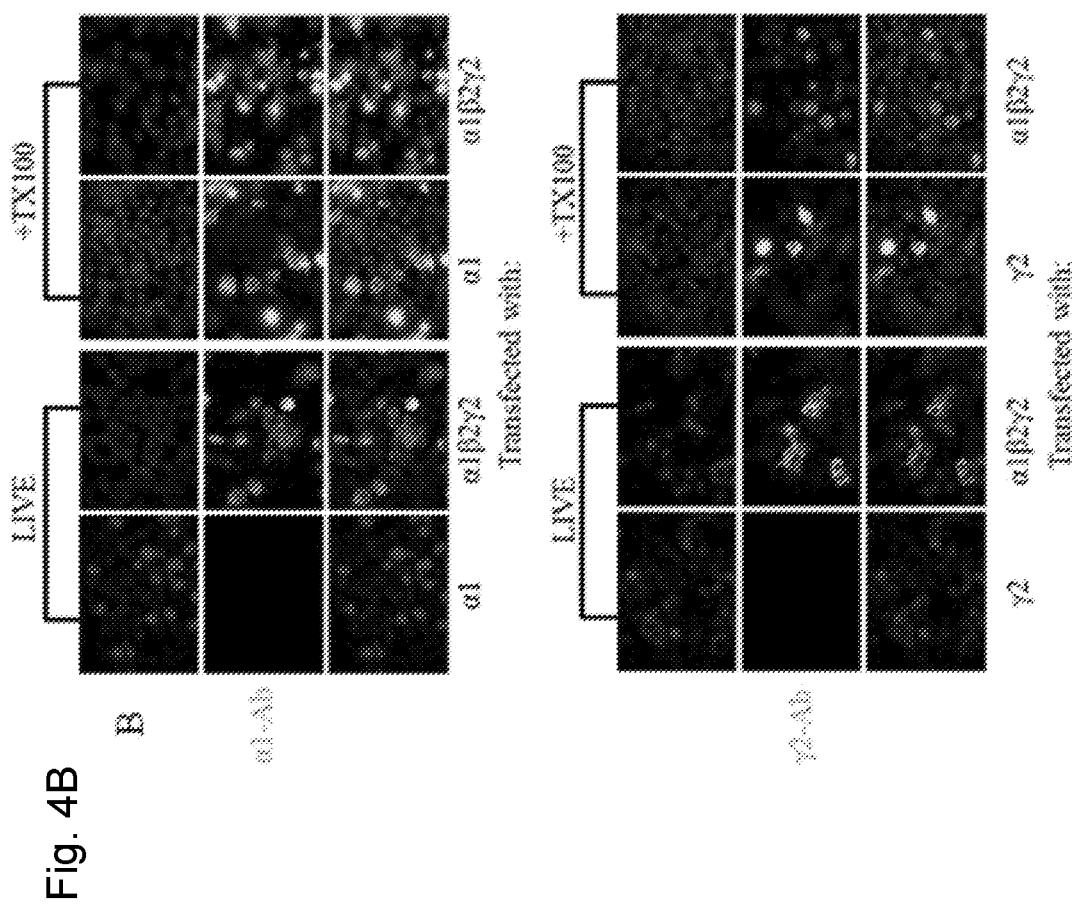
FIG. 4B shows GABA$_A$ receptor surface expression in HEK293 cells. HEK293 cells were transfected with single GABA$_A$R subunits (α1 or γ2) or with a combination of GABA$_A$R subunits (α1β2γ2) and probed with commercial antibodies against extracellular domains against the α1 or γ2 subunits. GABA$_A$R subunits were only expressed at the cell surface when expressed in combination and not when subunits were expressed alone; therefore all cell based assays used GABA$_A$R subunits expressed as heteropentamers.

A 72 year old female with a history of neuropsychological features with elements of obsessive-compulsive disorder and increased anxiety but without any psychosis was seen by a neurologist but there was no objective evidence of encephalitis and she returned to a Care Home. All routine antibody tests were negative (antibodies to NMDAR, LGI1, CASPR2, AMPAR, GABA$_B$R, Glycine-R), but her serum showed intense IgG labelling to the surface of both hippocampal and cortical neuronal cultures, indicating the presence of a potentially pathogenic antibody against a neuronal surface protein (FIG. 1A). To identify the antigen, live cortical neurons were incubated with patient sera and the antigen-IgG complex precipitated with Protein-G Sepharose beads. Mass spectrometry analysis of the immunoprecipitate identified peptides sequences corresponding to the α1 subunit of the GABA$_A$ receptor (FIG. 4A). The presence of the GABA$_A$ subunit in the immunoprecipitate was confirmed by western blotting with a commercial antibody against the α1 subunit, showing the presence of a 52 kDa protein band in the patient's immunoprecipitate but not in a healthy control immunoprecipitate (FIG. 1B).

Detection of GABA$_A$R-Antibodies in Patient Sera

Figure 1C:
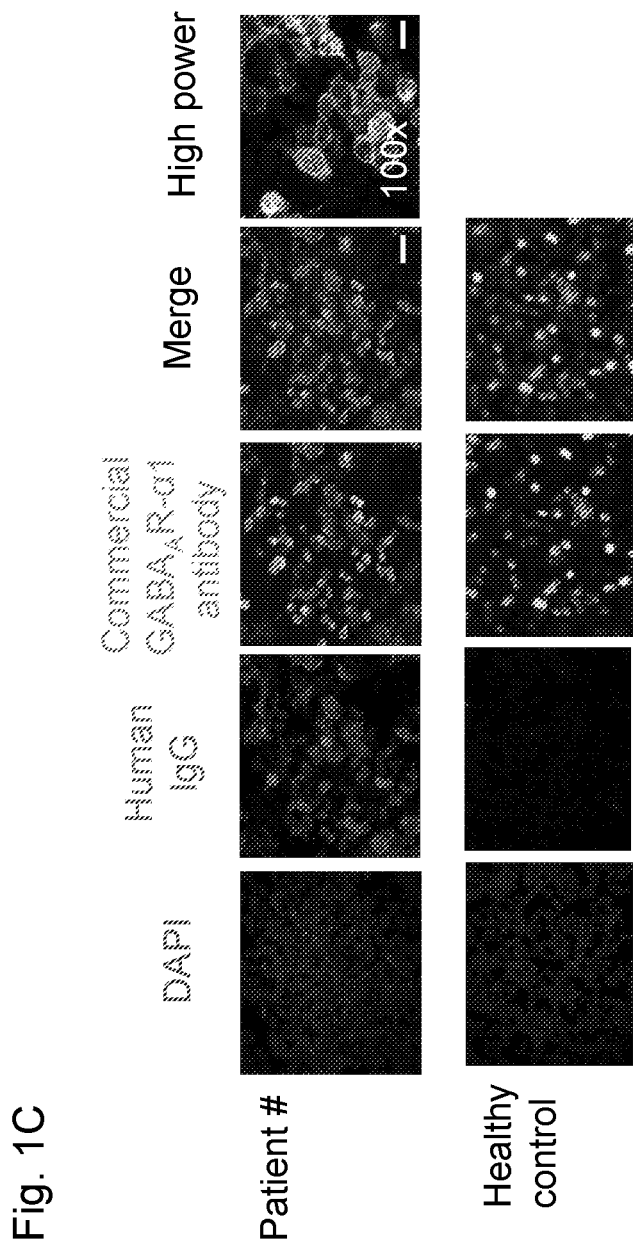

In vivo the GABA$_A$ receptor is assembled from multiple subunits (α1-6, β1-3, γ1-3, π, ε, θ and ρ1-3) which combine to form heteropentamers (2α's, 2β2's, 1 γ subunit) with a central pore (Tretter et al. 1997). The surface expression of individual monomeric GABA$_A$Rs (α1/β2/β3/γ2) as well as heteropentameric GABA$_A$Rs (α1β2γ2 subunits) was assessed using commercial antibodies against extracellular domains of the α1 and γ2 subunits; surface GABA$_A$R expression was only observed when cells were transfected with GABA$_A$R heteropentamers (α1β2γ2), although immunostaining of permeabilised fixed cells showed intracellular pools of the GABA$_A$R subunits when expressed individually (Supplementary FIG. 1B). To investigate the frequency of GABA$_A$ receptor antibodies, we established a cell-based assay (CBA), transfecting HEK cells with the α1β2γ2 subunits. The index patient's IgG bound to the surface of the GABA$_A$R-transfected cells, and IgG binding co-localised with commercial anti-GABA$_A$R α1 subunit (FIG. 1C).

Other Groups of Patients and Controls

Figure 1D:
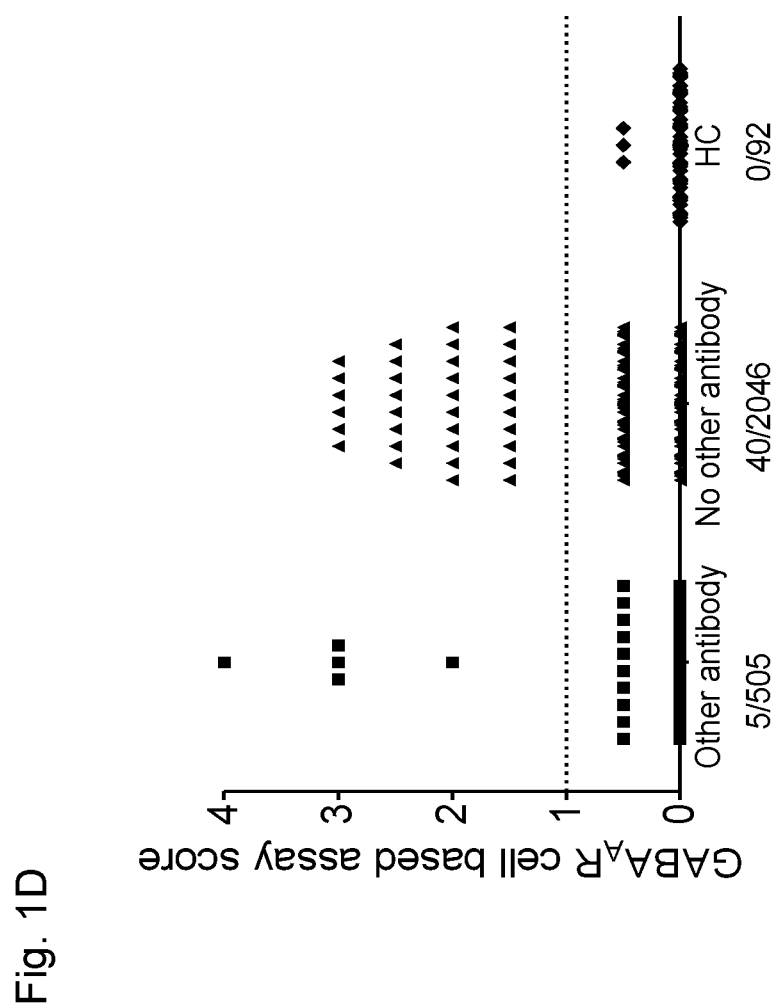

Serum from 92 healthy control samples did not bind to GABA$_A$R-cells (Table 1). The antibodies were detected in five of 505 (1%) sera positive for other antibodies. However, we found 40 (1.9%) GABA$_A$R antibody positive sera among 2153 samples previously found negative for other antibody tests (FIG. 1D). All 45 positive sera bound to live hippocampal neurons (data not shown).

Patient Antibodies Show Subunit Specific Reactivities

Figure 2B:
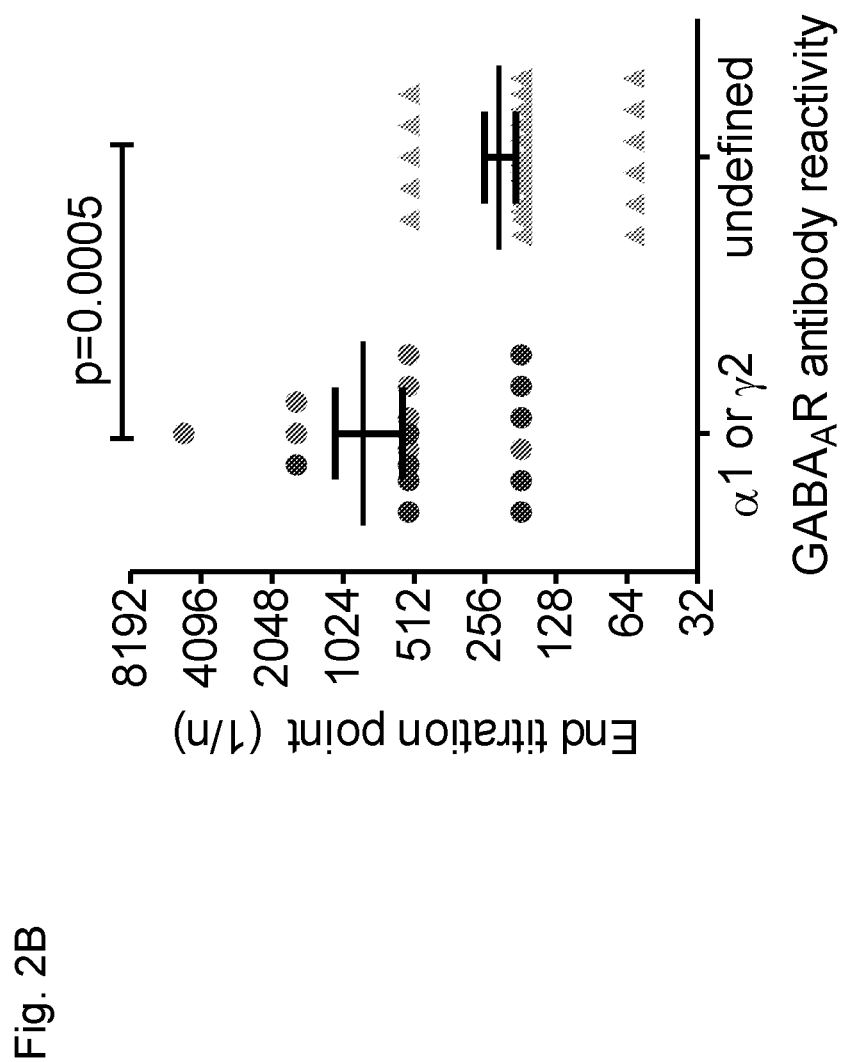
FIG. 2 shows specific GABA$_A$ receptor subunit-reactivities and immunoglobulin classes. A. In the index case (patient #1), substitution of the α1 subunit for either α2, α3,α5, ablated IgG reactivity to the GABA$_A$R-transfected cells, confirming that the α1 subunit was the antigenic target. α1-specific antibodies were observed in a further eight patients (20%). Case #11 illustrating the nine (20%) sera that bound only to GABA$_A$R formations containing the γ2 subunit, but not the γ1 subunit. Case #9 whose serum bound GABA$_A$R but did not show subunit specificity. B. Sera with subunit-specific GABA$_A$R antibodies (α1 and γ2) had significantly higher antibody titres than patients without a distinct subunit reactivity (Mann-Whitney, p=0.0005). C. Sera with specific α1 (n=9, red) or γ2-subunit (n=8, blue) antibody reactivities were always IgG1 ($^{16}/_{17}$) or IgG3 ($^{1}/_{17}$). Six patients also had additional low titre IgM antibodies. D. Sera without a defined GABA$_A$R subunit (green) antibody were predominantly IgM ($^{18}/_{20}$).

The 45 patients identified had antibodies that reacted with HEK cells transfected with the α1β2γ2 subunits of the GABA$_A$ receptor. Replacing α1 with α2, α3 or α5 subunits abolished the IgG binding to GABA$_A$R-transfected cells in Case #1 serum and a further eight samples tested. Replacing γ2 with γ1 abolished binding in a further nine sera (20%). Surprisingly, neither these substitutions nor replacing β2 with β3 reduced IgG binding in the remaining 28 sera, suggesting lack of subunit specificity. An example of subunit specific binding is shown in FIG. 2A. Notably, patients with α1 or γ2-specific antibodies had significantly higher antibody titres than patients lacking subunit specific reactivity (Mann-Whitney p=0.0005, FIG. 2B).

Subunit Specific Antibodies are Immunologically Distinct

Figure 2C:
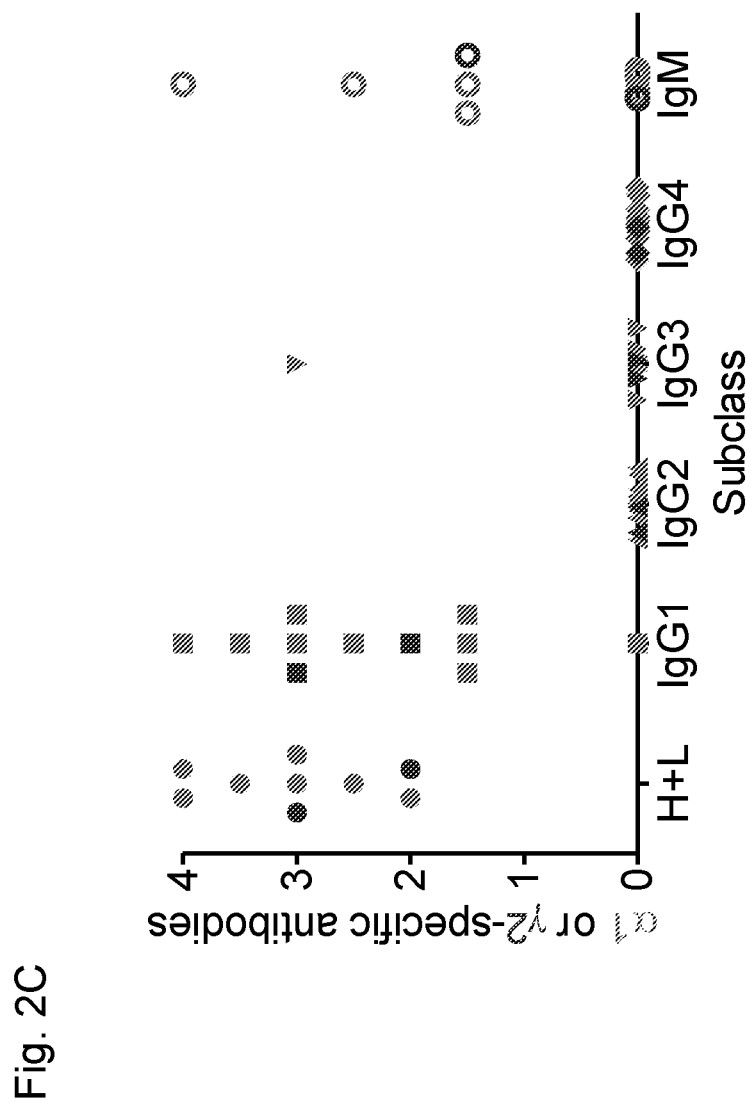
Figure 2D:
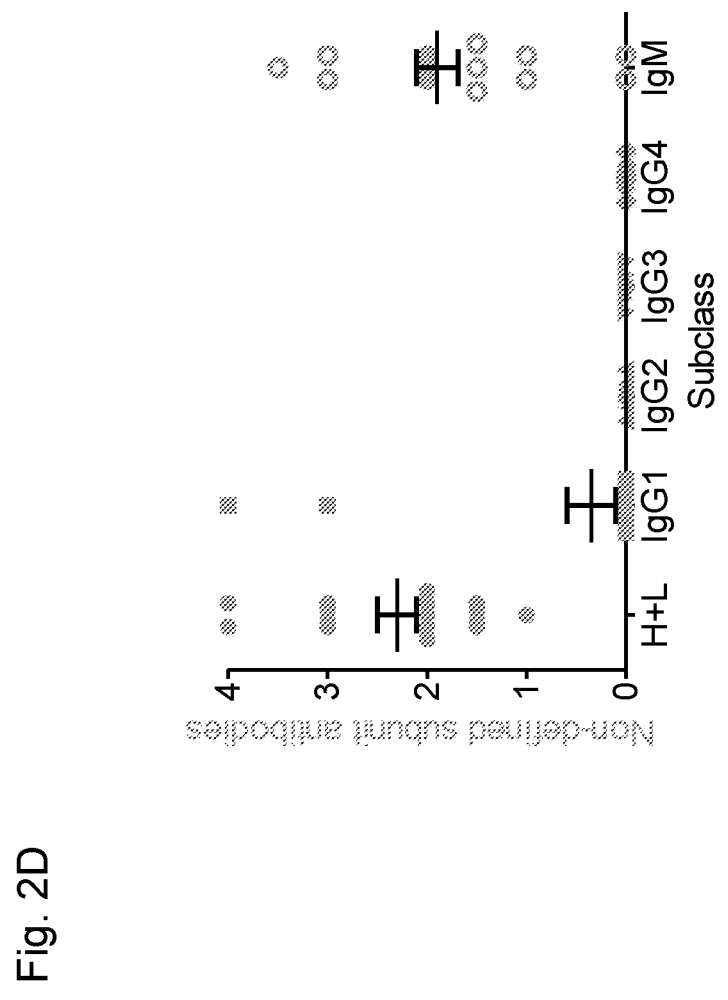

It was realised that the anti-human IgG used in the cell-based assays is directed against total IgG, which includes both heavy and light chains; this means that the anti-human IgG could pick up IgM antibodies by binding to their light chains. Using specific anti-IgG subclass and anti-IgM antibodies with 37 sera still available, it was found that only 19/37 (51.4%) patients had IgG1 (n=18) or IgG3 (n=1) GABA$_A$R antibodies (six also had IgM), while the remaining 18/37 sera had only IgM antibodies. Patients with α1 or γ2-specific GABA$_A$R-antibodies were always IgG1 (n=16/17) or IgG3 (n=1/17) compared with those without a defined subunit (n=2/20; p<0.0001 Fisher's exact test); conversely, the latter were more likely to have IgM-GABA$_A$R antibodies (18/20 versus 6/17 with a defined subunit reactivity; p=0.005, Fisher's exact test; FIG. 2C-D). The subunit and Ig specificities are indicated in Table 2.

Patient Antibodies Reduce GABA$_A$R Expression on the Neuronal Surface

Figure 3:
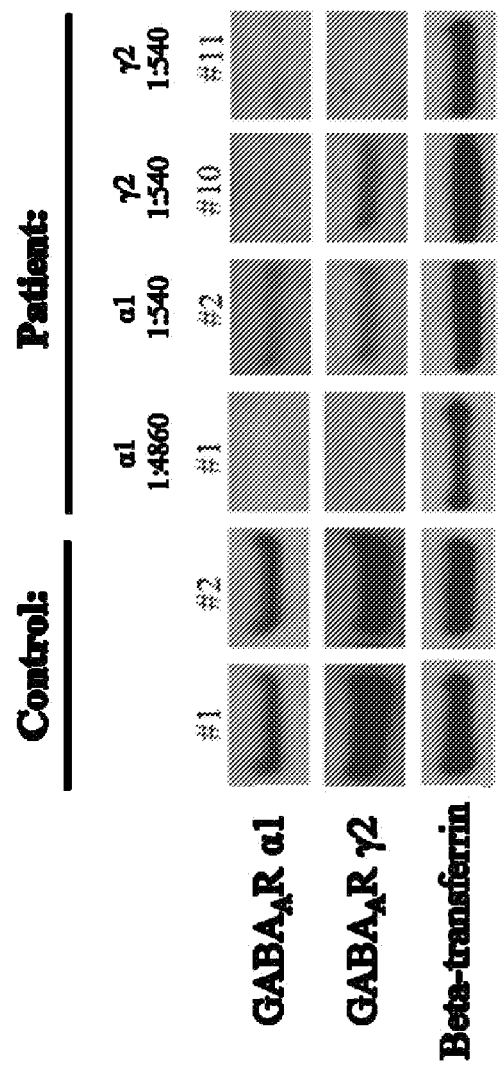
FIG. 3 shows patient antibodies reduce GABA$_A$R expression in neuronal cultures. Primary cortical neuronal cultures (day in vitro 7) were treated with serum (1:100) from GABA$_A$R-patients or healthy control for 72 hours. Western blot analysis showed that patient serum but not control, decrease GABA$_A$R levels (α1 and γ2) on the neuronal surface. Beta-transferrin is shown as a loading control.

To show potential pathogenicity, and as patient sera bound to primary cortical neurons, the effects of four IgG1 GABA$_A$R antibodies with high titres (endpoint dilutions 1:540-1:4860) on GABA$_A$R expression on hippocampal neurons in vitro (as in Hughes 2010, Lai 2010) was investigated. Neuronal cultures were exposed to patient or healthy control serum (1:100) for 72 hours. The GABA$_A$R expression was assessed by western blot of the neuron cell surface fraction, probing with commercial antibodies against GABA$_A$R α1 and γ2-subunits. All four patient sera caused a reduction in the surface expression of both α1 and γ2 subunits when compared to neurons treated with control sera (FIG. 3).

Clinical Phenotypes of 15 Patients with GABA$_A$ Receptor Antibodies

Clinical data (information requested in Table 2) for 15 patients, six with α1 and five with γ2 GABA$_A$R antibody specificity; four with unclear specificity are shown in Table 2. Overall, there were 6 females and 9 males, age range 13-72, median 47 years. The most common presenting features were seizures (n=8, 53.3%), memory impairment (n=7, 46.7%) with confusion or disorientation, or psychiatric features with hallucinations (n=3, 20%) or anxiety (n=3, 20%). One patient was catatonic and another had unexplained "non-epileptic" attacks. Another patient was undergoing treatment for non-Hodgkins' lymphoma and a 13 year old girl had a previously resected dysembryoplastic neuroepithelial tumour (DNET) with established neurodevelopment problems but presented with subacute onset of behavioural disturbance. MRI showed bilateral medial temporal lobe high signal in the patient with NHL who also had pleocytosis and oligoclonal bands; the diagnosis was probable paraneoplastic encephalitis with possible additional malignant infiltration of the brain. She responded to chemotherapy and immunotherapies. One other patient had unilateral high signal thought to relate to temporal lobe seizures rather than an inflammatory encephalitis. In the remaining patients there were non-specific white matter lesions in 2, but otherwise they were unremarkable (n=5) or not done (n=6). As the GABA$_A$R antibody was identified in many of these patients retrospectively, only 2/15 received immunotherapy.

Case 2

A 17-year old male, presented to psychiatrists with a one month history of forgetfulness, behavioural changes (disturbed thoughts; including harming others, requesting a sex-change and paranoid delusions, as well as attempts to self-harm). On examination he occasionally had mild tachycardia (up to 120/min), but neurological examination (MRI and two EEG's) was normal. He displayed intermittent drooling and long periods of staring; whilst at other times he was verbally unresponsive, sat abnormally still, with grimacing and posturing for more than one minute. Three months after presentation, the $GABA_AR$ antibody was detected in his serum (alpha 1 subunit; 1:540, IgG1-isotype) and a possible autoimmune aetiology was proposed. The patient received five days of plasma exchange, after which $GABA_AR$ antibodies were no longer detected in his serum and his frontal dysfunction and catatonia resolved within two weeks with subsequent further improvement.

4. Discussion

The $GABA_A$ receptor was identified as a new target and a cell based assay using HEK cells expressing heteropentameric $GABA_ARs$ was established. Testing sera from patients referred for other antibody tests identified a total of 45 with $GABA_AR$-antibodies. The antibodies in 40% of patients were IgG1 or IgG3, bound to $GABA_ARs$ containing α1 or γ2-subunits, and the four tested were able to reduce $GABA_AR$ expression on live cortical neurons indicating potential pathogenicity. In the remaining 60%, however, the titres were lower, the antibodies were mainly IgM and they did not show subunit specificity although they also bound to $GABA_ARs$ expressed in HEK cells, but not to other antigens, and to hippocampal neurons in culture. The clinical features of 15 representative patients included seizures, psychiatric and cognitive problems, and one had a known recent tumour. Two were treated systematically with immunotherapies and improved; the others were treated symptomatically. The $GABA_AR$ antibodies are relatively common, show evidence of pathogenicity, and were associated with seizure and behavioural phenotypes. However, the clinical features were variable, with one patient with a classical paraneoplastic limbic encephalitis.

In 18 patients, α1 or γ2 subunits were identified as the main targets. It was shown that both were able to reduce $GABA_AR$ complexes from the neuronal surface in vitro, most likely through antibody cross-linking as described for NMDAR and AMPAR-antibodies (Hughes et. al. 2010, Lai et. al. 2009), supporting the idea that these antibodies are pathogenic. Although the remaining 60% were low titre, mainly IgM, and did not show subunit specificity they were not observed in 92 healthy control sera.

The sera positive for $GABA_AR$ antibodies had been sent for a range of CNS antibody testing. Only 5/15 patients had epilepsy or limbic encephalitis, 8/15 had cognitive disturbances and although psychiatric features were common (7/15), the patients were given a range of tentative diagnoses, based on clinical and often limited MRI and CSF investigations, including neurodegenerative conditions and alcohol-related seizures. Although the histories were short in seven, there was little to suggest a classical immune-mediated disease such as limbic encephalitis or NMDAR-Ab encephalitis, and in two a functional or psychogenic condition was suspected. Nevertheless, the large number of referrals (over 4000 per year from the UK) and heterogeneity of the patients described here, illustrates the increasing interest in identifying antibodies in patients with subacute onset of unexplained seizures, cognitive or psychiatric features, and 12/15 of the neurologists indicated that they would have found it helpful if this antibody had been reported at the time of serum testing.

$GABA_A$ receptor antibodies were also identified recently in six patients with refractory status epilepticus or epilepsia partialis continua, binding to the α1 or β3 subunit of the $GABA_AR$ (Petit-Pedrol 2013) and in another 12 with a variety of phenotypes and lower titres. They did not look for γ2 subunit specificity. Moreover, they did not examine the Ig classes and subclasses. Both IgM and IgA NMDAR antibodies have previously been reported although the clinical relevance is not clear (Pruiss et. al. 2012) since the IgM antibodies identified here did bind to live neurons in culture, they may be pathogenic if they gain access to the CNS.

Future prospective studies, detecting $GABA_AR$ antibodies at onset, testing CSF and judicious use of immunotherapy, with in vitro and in vivo experiments comparing the effects of IgG and IgM antibodies, will be important in determining their full clinical relevance. Recognition that a specific potentially pathogenic antibody can associate with clinical features that are more diverse and less syndromic than the well-known autoimmune encephalitis syndromes could have implications for future studies of unexplained central nervous system disease.

TABLE 1 summary of serum samples screened for $GABA_AR$-antibodies

| Sera examined | Number positive for $GABA_AR$ antibody |
|---|---|
| Healthy control | 0/92 (0%) |
| Sera from patients positive for other neuronal antibodies: VGKC-complex, VGCC, NMDAR, GlyR, LGI1, CASPR2, Contactin-2, AMPAR, $GABA_B$ | 5/505 (1.05%) |
| Samples sent for testing for one or more of the above antibodies that were negative | 40/2153 (1.9%) |
| Total sera positive | 45/2657 (1.8%) |

TABLE 2

Clinical data of 15 patients with serum $GABA_AR$-antibodies

| | Laboratory data | | | Questionnaire | | |
|---|---|---|---|---|---|---|
| Case | Titre, subunit, Ab subclass | Sex, age, duration at testing | Co-morbidities or other antibodies | confusion or other clinical features at presentation | Amnesia, disorientation, movement disorders, neurological features or other diseases | Other MRI, CSF, other investigations |
| 1 | 1:4860 α1 IgG1+ IgM− | F, 72, | VGKC-complex 1938 pM | Increasing obsessive-compulsive disorder and increased anxiety. Facial twitches. | Mild myokymia and head tremor | Not done |

TABLE 2-continued

Clinical data of 15 patients with serum GABA$_A$R-antibodies

| # | Titer/Subclass | Sex, Age, Duration | Other | Symptoms | Comorbidities | Imaging/EEG |
|---|---|---|---|---|---|---|
| 2 | 1:540 α1 IgG1+ IgM+ | M, 17 1 month | None | Forgetfulness, behavioural changes, disturbed thought, incontinence, catatonic, grimacing, posturing | Bush Frances Catatonia Rating Scale indicated moderate severity | MRI and two EEG's normal |
| 3 | 1:180 α1 IgG1+ IgM+ | M, 56 1 month | None | Visual unformed hallucinations with eye and head deviation up to 10 per hour. No amnesia, psychosis or movement disorders | Type 2 DM, coronary artery stent, hypertension | MRI FLAIR lesion after seizures, resolved. CSF normal. No tumour. EEG: focal visual partial seizures leading to head/eye deviation |
| 4 | 1:540 α1 IgG1+ IgM− | M, 47 12 months | HIV, on cART. Splenectomy for ITP. | Impaired memory, verbal fluency, word-finding; depression; GTCS. Nil else | Previous weight loss, plateaued | No abnormalities found on MRI, CSF, EEG |
| 5 | 1:1620 α1 IgG1+ IgM− | F, 19 1 week | NMDAR 1:540 | GTCS following drugs and sleep deprivation | None | Awaited EEG |
| 6 | 1:540 α1 IgG3+ IgM− | M, 36 1.2 years | Chronic back pain | Weekly loss of conciousness for up to one hour as if asleep | None | MRI, normal at Swindon CSF not done |
| 10 | 1:540 γ2, IgG1+ IgM+ | M, 47, 1-2 m | Gluten sensitivity VGKC, NMDAR negative | Severe amnesia, confusion, hallucinations, seizures, ataxia | Global weakness with axonal neuropathy | Cerebellum abnormal MRS. Epileptic activity on EEG |
| 11 | 1:540 γ2 IgG1+ IgM+ | F, 13, 4 m | VGKC, NMDAR negative | Disorientation, behavioural change, violence, refusal to walk or talk, absences | DNET resected previously. Epilepsy, severe learning disability, hypothyroidism | Nocturnal GTCS - EEG shows no NCSE. Tumour size unchanged, no other abnormalities, CSF not done |
| 12 | 1:1620 γ2 IgG1+ IgM− | M 62, 3 y | None VGKC, NMDAR negative | Amnesia only | None | MRI, few scattered WM lesions. no other significant findings |
| 13 | 1:180 γ2 Subclass not available | F, 56, 2/3 m | Anxiety, dizziness, dysphagia, leg weak NMDAR negative | appendicular and axial dyskinesias (choreiform) at rest | Long-standing anxiety | MRI Brain caudate heads looked small, no EEG done, CSF normal |
| 14 | 1:540 γ2 IgG1+ IgM− | F, 47, 18 m | None GAD, GLYR, NMDAR, AMPAR, GABA$_B$ negative | Marked anterograde amnesia and selective spatial disorientation, with retained retrograde memory. GTCS. No other seizures or myoclonus. No hallucinations. | Increasing nocturnal seizures with partial response to maximum CBZ and VPA. | EEG Generalized tonic pattern, no focal. Intermittent and repeated spike/sharp wave activity on sleep-deprived EEG. Left fronto-temporal region, normal background. |
| 15 | 1:60 Undefined IgG− IgM+ | M, 68, 2 m | Ca prostate VGKC, NMDAR negative | Amnesia, self-neglect, depression, GTCS with status epilepticus, and excessive sleepiness | Epilepsy, subarachnoid haemorrhage | CT Evidence of craniotomy and clip. R frontal and temporal lobe gliosis, dilatation of R ventricle. Minor periventricular WM only. CSF, EEG not done. |
| 7 | 1:180 Undefined IgG− IgM+ | M, 27, 9 y | NMDAR negative | Anxiety, poor concentration, hallucinations | | Not done |
| 8 | 1:180 Undefined IgG− IgM+ | F, 65, 1 m | NMDAR negative | Headache, confusion, memory loss, anxiety | Non-Hodgkins lymphoma | MRI both temporal lobes signal change extending to amygdalae; raised lymphocytes aad OCBS |

TABLE 2-continued

Clinical data of 15 patients with serum GABA$_A$R-antibodies

| Case | Titre, subunit, Ab subclass | Sex, age, duration at testing | Referring neurologists' diagnosis | Immunotherapy given and result | Would a positive antibody test have been helpful? |
|---|---|---|---|---|---|
| 9 | 1:540 Undefined IgG− IgM+ | M, 62, 15 m | Hypertension hyperlipidaemia, prostatism NMDAR, GAD, VGKC-complex antibodies 550 pM | Partial complex seizures, no amnesia, psychiatric, MD, ataxia | None | MRI, few white dots only |

| | Laboratory data | | Questionnaire | | |
|---|---|---|---|---|---|
| Case | Titre, subunit, Ab subclass | Sex, age, duration at testing | Referring neurologists' diagnosis | Immunotherapy given and result | Would a positive antibody test have been helpful? |
| 1 | 1:4860 α1 IgG1+ IgM− | F, 72, | Unclear | None given. Patient reluctant to attend hospital again. | Yes |
| 2 | 1:540 α1 IgG1+ IgM+ | M, 17 1 month | Catatonia of unknown aetiology | One course PLEX. Symptoms resolved in two weeks. | Yes |
| 3 | 1:180 α1 IgG1+ IgM+ | M, 56 1 month | Partial status epilepticus of unknown aetiology | None given. AEDs only | Yes |
| 4 | 1:540 α1 IgG1+ IgM− | M, 47 12 months | Possible neurodgenerative disorder | None given | Yes |
| 5 | 1:1620 α1 IgG1+ IgM− | F, 19 1 week | Drugs/alcohol related seizures, no other cause? | Keppra only required | Yes |
| 6 | 1:540 α1 IgG3+ IgM− | M, 36 12 years | Non-epileptic attacks | None given | Unsure |
| 10 | 1:540 γ2, IgG1+ IgM+ | M, 47, 1-2 m | Possible celiac-associated autoimmune encephalitis but alcohol contributory | None given | Yes |
| 11 | 1:540 γ2 IgG1+ IgM+ | F, 13, 4 m | Possible psychological disorder on background of DNET | None given | Yes |
| 12 | 1:1620 γ2 IgG1+ IgM− | M 62, 3 y | Mild cognitive impairment | None given | Unsure |
| 13 | 1:180 γ2 Subclass not available | F, 56, 2/3 m | Acute chorea, ?autoimmune. ? Huntington's disease | None given | Yes, but Huntington's gene positive subsequently |
| 14 | 1:540 γ2 IgG1+ IgM− | F, 47, 18 m | Late-onset focal epilepsy or limbic encephalitis | None given Seizures AED resistant | Yes |
| 15 | 1:60 Undefined IgG− IgM+ | M, 68, 2 m | Delirium on the background of dementia | None given | Not stated |
| 7 | 1:180 Undefined IgG− IgM+ | M, 27, 9 y | Paranoid schizophrenia | None given Clozapine only | Unsure |
| 8 | 1:180 Undefined IgG− IgM+ | F, 65, 1 m | NHL with CNS infiltration and probable paraneoplastic autoimmune encephalitis | Steroids, intrathecal chemotherapy | Yes |

TABLE 2-continued

Clinical data of 15 patients with serum GABA$_A$R-antibodies

| | | | | | |
|---|---|---|---|---|---|
| 9 | 1:540 Undefined IgG− IgM+ | M, 62, 15 m | Focal epilepsy | None given | Yes |

DNET = Dysembryoplastic neuroepithelial tumour

TABLE 3

GABA$_A$R cDNA

| GABA$_A$R subunit | Transfection vector |
|---|---|
| α1 | pcDNA3.1 hygro+ |
| α2 | pcDNA3.1 hygro+ |
| α3 | pIRES2-AcGFP1 |
| α5 | pcDNA3.1 hygro+ |
| β2 | pcDNA3.1 hygro+ |
| β3 | pCMV-Sport6 |
| γ1 | pcDNA3.1 hygro+ |
| γ2 | pcDNA3.1 hygro+ |

TABLE 4

GABA$_A$R-cell surface expression; tested with commercial antibodies against extracellular domains

| HEK293 cells transfected with: | Surface expression |
|---|---|
| α1 | No |
| β2 | No |
| β3 | No |
| γ2 | No |
| α1β2γ2 | α1 - Yes<br>β2 - No<br>γ2 - Yes |
| α1β3γ2 | α1 - Yes<br>γ2 - Yes |
| α3β2γ2 | α3 - Yes<br>γ2 - Yes |

5. References

Akbarian, S. et al., 1995. GABA$_A$ receptor subunit gene expression in human prefrontal cortex: comparison of schizophrenics and controls. *Cerebral cortex* (New York, N.Y. 1991), 5(6), pp. 550-60.

Brenner, T. et al., 2013. Prevalence of neurologic autoantibodies in cohorts of patients with new and established epilepsy. *Epilepsia*, 54(6), pp. 1028-35.

Dalmau, J et al., 2007. Paraneoplastic anti-N-methyl-D-aspartate receptor encephalitis associated with ovarian teratoma. *Annals of.*

Dalmau, Josep et al., 2008. Anti-NMDA-receptor encephalitis: case series and analysis of the effects of antibodies. *The Lancet Neurology*, 7(12), pp. 1091-1098.

Hevers, W. & Lüddens, H., 1998. The diversity of GABA$_A$ receptors. Pharmacological and electrophysiological properties of GABA$_A$ channel subtypes. *Molecular neurobiology*, 18(1), pp. 35-86.

Hughes, E. G. et al., 2010. Cellular and Synaptic Mechanisms of Anti-NMDA Receptor Encephalitis. *Journal of Neuroscience*, 30(17), pp. 5866-5875.

Irani, S. R. et al., 2010a. N-methyl-D-aspartate antibody encephalitis: temporal progression of clinical and paraclinical observations in a predominantly non-paraneoplastic disorder of both sexes. *Brain*, 133(6), pp. 1655-1667.

Irani, S. et al., 2011. Faciobrachial dystonic seizures precede Lgi1 antibody limbic encephalitis. *Annals of.*

Irani, Sarosh R et al., 2010b. Antibodies to Kv1 potassium channel-complex proteins leucine-rich, glioma inactivated 1 protein and contactin-associated protein-2 in limbic encephalitis, Morvan's syndrome and acquired neuromyotonia. *Brain: a journal of neurology*, 133(9), pp. 2734-48.

Lai, M. et al., 2009. AMPA receptor antibodies in limbic encephalitis alter synaptic receptor location. *Annals of neurology*, 65(4), pp. 424-434.

Lancaster, E. et al., 2010. Antibodies to the GABAB receptor in limbic encephalitis with seizures: case series and characterisation of the antigen. *The Lancet Neurology*, 9(1), pp. 67-76.

Limon, A., Reyes-Ruiz, J. M. & Miledi, R., 2012. Loss of functional GABA(A) receptors in the Alzheimer diseased brain. *Proceedings of the National Academy of Sciences of the United States of America*, 109(25), pp. 10071-6.

Macdonald, R., Kang, J. & Gallagher, M., 2010. Mutations in GABA$_A$ receptor subunits associated with genetic epilepsies. *The Journal of Physiology*, 588(11), pp. 1861-1869.

McKernan, R. M. & Whiting, P. J., 1996. Which GABA$_A$-receptor subtypes really occur in the brain? *Trends in Neurosciences*, 19(4), pp. 139-43.

Petit-Pedrol, M. et al., 2014. Encephalitis with refractory seizures, status epilepticus, and antibodies to the GABA$_A$ receptor: a case series, characterisation of the antigen, and analysis of the effects of antibodies. *Lancet neurology*, 13(3), pp. 276-86.

Prüss, H, Höltje, M., Maier, N., Gomez, A. & Buchert, R., 2012a. IgA NMDA receptor antibodies are markers of synaptic immunity in slow cognitive impairment. *Neurology.*

Prüss, H, Höltje, M., Maier, N., Gomez, A., Buchert, R., et al., 2012b. IgA NMDA receptor antibodies are markers of synaptic immunity in slow cognitive impairment. *Neurology*, 78(22), pp. 1743-53.

Prüss, Harald et al., 2012c. N-methyl-D-aspartate receptor antibodies in herpes simplex encephalitis. *Annals of neurology*, 72(6), pp. 902-11.

Rose, N. R. & Bona, C., 1993. Defining criteria for autoimmune diseases (Witebsky's postulates revisited). *Immunology today*, 14(9), p.426.

Steiner, J. et al., 2013. Increased prevalence of diverse N-methyl-D-aspartate glutamate receptor antibodies in patients with an initial diagnosis of schizophrenia: specific relevance of IgG NR1a antibodies for distinction from N-methyl-D-aspartate glutamate receptor encephalitis. *JAMA psychiatry*, 70(3), pp. 271-8.

Tiihonen, J. et al., 1997. Cerebral benzodiazepine receptor binding and distribution in generalized anxiety disorder: a fractal analysis. *Molecular Psychiatry*, 2(6), pp. 463-71.

Titulaer, M. J. et al., 2013. Treatment and prognostic factors for long-term outcome in patients with anti-NMDA receptor encephalitis: an observational cohort study. *Lancet neurology*, 12(2), pp. 157-65.

Tretter, V. et al., 1997. Stoichiometry and assembly of a recombinant GABA$_A$ receptor subtype. *The Journal of neuroscience: the official journal of the Society for Neuroscience*, 17(8), pp. 2728-37.

Tsutsui, K. et al., 2012. Anti-NMDA-receptor antibody detected in encephalitis, schizophrenia, and narcolepsy with psychotic features. *BMC psychiatry*, 12, p.37.

Tüzün, E. et al., 2009. Evidence for antibody-mediated pathogenesis in anti-NMDAR encephalitis associated with ovarian teratoma. *Acta neuropathologica*, 118(6), pp. 737-43.

Vincent, A. et al., 2004. Potassium channel antibody-associated encephalopathy: a potentially immunotherapy-responsive form of limbic encephalitis. *Brain: a journal of neurology*, 127(Pt 3), pp. 701-12.

The invention claimed is:

1. A method for detecting the presence of an autoantibody directed against the γ2 subunit of the gamma-aminobutyric acid A receptor (GABA$_A$R) in an individual suspected of having a neurological disease, the method comprising:
   (a) contacting a sample obtained from the individual with GABA$_A$ receptors expressed in a cell, wherein the γ2 subunit is expressed alongside the α1 and β2 or β3 subunits to form a heteropentameric in vivo form of the GABA$_A$R in the cellular membrane of the cell; and
   (b) detecting the binding of one or more autoantibodies in the sample to the γ2 subunit of the GABA$_A$R.

2. The method according to claim 1, wherein:
   (i) the GABA$_A$R comprises the α1 and γ2 subunits;
   (ii) the GABA$_A$R comprises 2 α1, 2 β2 and 1 γ2 subunits;
   (iii) the GABA$_A$R comprises α1, β3 and γ2 subunits; and/or
   (iv) the autoantibodies are IgG.

3. The method according to claim 2, wherein the method further comprises determining the IgG subclass of the detected autoantibodies, wherein said autoantibodies are determined to be IgG1 or IgG3.

4. The method according to claim 1, wherein the neurological disease is a central nervous system (CNS) disease.

5. The method according to claim 4, wherein the CNS disease is autoimmune encephalitis, limbic encephalitis, status epilepticus, epilepsy, a movement disorder or a psychiatric disorder.

6. The method according to claim 4, wherein the CNS disease is associated with seizures, amnesia, behavioural changes, hallucinations, anxiety, sleep disorders, stiffness and/or rigidity.

7. The method according to claim 5, wherein the psychiatric disorder is anxiety, psychosis or catatonia.

8. The method according to claim 1, wherein the measuring comprises an enzyme-linked immunosorbent assay (ELISA), radioimmunoassay, luminescence assay, competition assay, inhibition assay, sandwich assay, fluorescent microscopy, microarray or fluorescence-activated cell sorting (FACS) analysis.

9. The method according to claim 1, wherein when one or more autoantibodies to the γ2 subunit of the $GABA_AR$ are detected the method further comprises administering to the individual a therapeutically effective amount of a suitable therapy.

10. The method according to claim 9, wherein the suitable therapy is immunotherapy with steroids, plasma exchange, intravenous immunoglobulins, immunosuppressive drugs, steroid-sparing drugs, cyclophosphamide, cyclosporine and therapeutic monoclonal antibodies.

\* \* \* \* \*

SEQUENCE LISTING

```
<160> NUMBER OF SEQ ID NOS: 9

<210> SEQ ID NO 1
<211> LENGTH: 467
<212> TYPE: PRT
<213> ORGANISM: homo sapiens

<400> SEQUENCE: 1

Met Ser Ser Pro Asn Ile Trp Ser Thr Gly Ser Ser Val Tyr Ser Thr
1               5                   10                  15

Pro Val Phe Ser Gln Lys Met Thr Val Trp Ile Leu Leu Leu Leu Ser
                20                  25                  30

Leu Tyr Pro Gly Phe Thr Ser Gln Lys Ser Asp Asp Tyr Glu Asp
            35                  40                  45

Tyr Ala Ser Asn Lys Thr Trp Val Leu Thr Pro Lys Val Pro Glu Gly
        50                  55                  60

Asp Val Thr Val Ile Leu Asn Asn Leu Leu Glu Gly Tyr Asp Asn Lys
65                  70                  75                  80

Leu Arg Pro Asp Ile Gly Val Lys Pro Thr Leu Ile His Thr Asp Met
                85                  90                  95

Tyr Val Asn Ser Ile Gly Pro Val Asn Ala Ile Asn Met Glu Tyr Thr
                100                 105                 110

Ile Asp Ile Phe Phe Ala Gln Met Trp Tyr Asp Arg Arg Leu Lys Phe
            115                 120                 125

Asn Ser Thr Ile Lys Val Leu Arg Leu Asn Ser Asn Met Val Gly Lys
        130                 135                 140

Ile Trp Ile Pro Asp Thr Phe Phe Arg Asn Ser Lys Lys Ala Asp Ala
145                 150                 155                 160

His Trp Ile Thr Thr Pro Asn Arg Met Leu Arg Ile Trp Asn Asp Gly
                165                 170                 175

Arg Val Leu Tyr Ser Leu Arg Leu Thr Ile Asp Ala Glu Cys Gln Leu
                180                 185                 190

Gln Leu His Asn Phe Pro Met Asp Glu His Ser Cys Pro Leu Glu Phe
            195                 200                 205

Ser Ser Tyr Gly Tyr Pro Arg Glu Glu Ile Val Tyr Gln Trp Lys Arg
        210                 215                 220

Ser Ser Val Glu Val Gly Asp Thr Arg Ser Trp Arg Leu Tyr Gln Phe
225                 230                 235                 240

Ser Phe Val Gly Leu Arg Asn Thr Thr Glu Val Val Lys Thr Thr Ser
                245                 250                 255

Gly Asp Tyr Val Val Met Ser Val Tyr Phe Asp Leu Ser Arg Arg Met
                260                 265                 270

Gly Tyr Phe Thr Ile Gln Thr Tyr Ile Pro Cys Thr Leu Ile Val Val
            275                 280                 285

Leu Ser Trp Val Ser Phe Trp Ile Asn Lys Asp Ala Val Pro Ala Arg
        290                 295                 300
```

```
Thr Ser Leu Gly Ile Thr Val Leu Thr Met Thr Thr Leu Ser Thr
305                 310                 315                 320

Ile Ala Arg Lys Ser Leu Pro Lys Val Ser Tyr Val Thr Ala Met Asp
                325                 330                 335

Leu Phe Val Ser Val Cys Phe Ile Phe Val Phe Ser Ala Leu Val Glu
            340                 345                 350

Tyr Gly Thr Leu His Tyr Phe Val Ser Asn Arg Lys Pro Ser Lys Asp
        355                 360                 365

Lys Asp Lys Lys Lys Asn Pro Ala Pro Thr Ile Asp Ile Arg Pro
370                 375                 380

Arg Ser Ala Thr Ile Gln Met Asn Asn Ala Thr His Leu Gln Glu Arg
385                 390                 395                 400

Asp Glu Glu Tyr Gly Tyr Glu Cys Leu Asp Gly Lys Asp Cys Ala Ser
                405                 410                 415

Phe Phe Cys Cys Phe Glu Asp Cys Arg Thr Gly Ala Trp Arg His Gly
            420                 425                 430

Arg Ile His Ile Arg Ile Ala Lys Met Asp Ser Tyr Ala Arg Ile Phe
        435                 440                 445

Phe Pro Thr Ala Phe Cys Leu Phe Asn Leu Val Tyr Trp Val Ser Tyr
450                 455                 460

Leu Tyr Leu
465

<210> SEQ ID NO 2
<211> LENGTH: 456
<212> TYPE: PRT
<213> ORGANISM: homo sapiens

<400> SEQUENCE: 2

Met Arg Lys Ser Pro Gly Leu Ser Asp Cys Leu Trp Ala Trp Ile Leu
1               5                   10                  15

Leu Leu Ser Thr Leu Thr Gly Arg Ser Tyr Gly Gln Pro Ser Leu Gln
            20                  25                  30

Asp Glu Leu Lys Asp Asn Thr Thr Val Phe Thr Arg Ile Leu Asp Arg
        35                  40                  45

Leu Leu Asp Gly Tyr Asp Asn Arg Leu Arg Pro Gly Leu Gly Glu Arg
    50                  55                  60

Val Thr Glu Val Lys Thr Asp Ile Phe Val Thr Ser Phe Gly Pro Val
65                  70                  75                  80

Ser Asp His Asp Met Glu Tyr Thr Ile Asp Val Phe Phe Arg Gln Ser
                85                  90                  95

Trp Lys Asp Glu Arg Leu Lys Phe Lys Gly Pro Met Thr Val Leu Arg
            100                 105                 110

Leu Asn Asn Leu Met Ala Ser Lys Ile Trp Thr Pro Asp Thr Phe Phe
        115                 120                 125

His Asn Gly Lys Lys Ser Val Ala His Asn Met Thr Met Pro Asn Lys
    130                 135                 140

Leu Leu Arg Ile Thr Glu Asp Gly Thr Leu Leu Tyr Thr Met Arg Leu
145                 150                 155                 160

Thr Val Arg Ala Glu Cys Pro Met His Leu Glu Asp Phe Pro Met Asp
                165                 170                 175

Ala His Ala Cys Pro Leu Lys Phe Gly Ser Tyr Ala Tyr Thr Arg Ala
            180                 185                 190

Glu Val Val Tyr Glu Trp Thr Arg Glu Pro Ala Arg Ser Val Val Val
        195                 200                 205
```

Ala Glu Asp Gly Ser Arg Leu Asn Gln Tyr Asp Leu Leu Gly Gln Thr
                210                 215                 220

Val Asp Ser Gly Ile Val Gln Ser Ser Thr Gly Glu Tyr Val Val Met
225                 230                 235                 240

Thr Thr His Phe His Leu Lys Arg Lys Ile Gly Tyr Phe Val Ile Gln
                245                 250                 255

Thr Tyr Leu Pro Cys Ile Met Thr Val Ile Leu Ser Gln Val Ser Phe
                260                 265                 270

Trp Leu Asn Arg Glu Ser Val Pro Ala Arg Thr Val Phe Gly Val Thr
                275                 280                 285

Thr Val Leu Thr Met Thr Thr Leu Ser Ile Ser Ala Arg Asn Ser Leu
                290                 295                 300

Pro Lys Val Ala Tyr Ala Thr Ala Met Asp Trp Phe Ile Ala Val Cys
305                 310                 315                 320

Tyr Ala Phe Val Phe Ser Ala Leu Ile Glu Phe Ala Thr Val Asn Tyr
                325                 330                 335

Phe Thr Lys Arg Gly Tyr Ala Trp Asp Gly Lys Ser Val Val Pro Glu
                340                 345                 350

Lys Pro Lys Lys Val Lys Asp Pro Leu Ile Lys Asn Asn Thr Tyr
                355                 360                 365

Ala Pro Thr Ala Thr Ser Tyr Thr Pro Asn Leu Ala Arg Gly Asp Pro
370                 375                 380

Gly Leu Ala Thr Ile Ala Lys Ser Ala Thr Ile Glu Pro Lys Glu Val
385                 390                 395                 400

Lys Pro Glu Thr Lys Pro Pro Glu Pro Lys Lys Thr Phe Asn Ser Val
                405                 410                 415

Ser Lys Ile Asp Arg Leu Ser Arg Ile Ala Phe Pro Leu Leu Phe Gly
                420                 425                 430

Ile Phe Asn Leu Val Tyr Trp Ala Thr Tyr Leu Asn Arg Glu Pro Gln
                435                 440                 445

Leu Lys Ala Pro Thr Pro His Gln
                450                 455

<210> SEQ ID NO 3
<211> LENGTH: 512
<212> TYPE: PRT
<213> ORGANISM: homo sapiens

<400> SEQUENCE: 3

Met Trp Arg Val Arg Lys Arg Gly Tyr Phe Gly Ile Trp Ser Phe Pro
1                 5                   10                  15

Leu Ile Ile Ala Ala Val Cys Ala Gln Ser Val Asn Asp Pro Ser Asn
                20                  25                  30

Met Ser Leu Val Lys Glu Thr Val Asp Arg Leu Leu Lys Gly Tyr Asp
                35                  40                  45

Ile Arg Leu Arg Pro Asp Phe Gly Gly Pro Pro Val Ala Val Gly Met
                50                  55                  60

Asn Ile Asp Ile Ala Ser Ile Asp Met Val Ser Glu Val Asn Met Asp
65                  70                  75                  80

Tyr Thr Leu Thr Met Tyr Phe Gln Gln Ala Trp Arg Asp Lys Arg Leu
                85                  90                  95

Ser Tyr Asn Val Ile Pro Leu Asn Leu Thr Leu Asp Asn Arg Val Ala
                100                 105                 110

Asp Gln Leu Trp Val Pro Asp Thr Tyr Phe Leu Asn Asp Lys Lys Ser
                115                 120                 125

-continued

```
Phe Val His Gly Val Thr Val Lys Asn Arg Met Ile Arg Leu His Pro
130                 135                 140

Asp Gly Thr Val Leu Tyr Gly Leu Arg Ile Thr Thr Ala Ala Cys
145                 150                 155                 160

Met Met Asp Leu Arg Arg Tyr Pro Leu Asp Glu Gln Asn Cys Thr Leu
                165                 170                 175

Glu Ile Glu Ser Tyr Gly Tyr Thr Thr Asp Ile Glu Phe Tyr Trp
            180                 185                 190

Arg Gly Asp Asp Asn Ala Val Thr Gly Val Thr Lys Ile Glu Leu Pro
        195                 200                 205

Gln Phe Ser Ile Val Asp Tyr Lys Leu Ile Thr Lys Lys Val Val Phe
210                 215                 220

Ser Thr Gly Ser Tyr Pro Arg Leu Ser Leu Ser Phe Lys Leu Lys Arg
225                 230                 235                 240

Asn Ile Gly Tyr Phe Ile Leu Gln Thr Tyr Met Pro Ser Ile Leu Ile
                245                 250                 255

Thr Ile Leu Ser Trp Val Ser Phe Trp Ile Asn Tyr Asp Ala Ser Ala
            260                 265                 270

Ala Arg Val Ala Leu Gly Ile Thr Thr Val Leu Thr Met Thr Thr Ile
        275                 280                 285

Asn Thr His Leu Arg Glu Thr Leu Pro Lys Ile Pro Tyr Val Lys Ala
290                 295                 300

Ile Asp Met Tyr Leu Met Gly Cys Phe Val Phe Val Phe Met Ala Leu
305                 310                 315                 320

Leu Glu Tyr Ala Leu Val Asn Tyr Ile Phe Phe Gly Arg Gly Pro Gln
                325                 330                 335

Arg Gln Lys Lys Ala Ala Glu Lys Ala Ser Ala Asn Asn Glu Lys
            340                 345                 350

Met Arg Leu Asp Val Asn Lys Ile Phe Tyr Lys Asp Ile Lys Gln Asn
        355                 360                 365

Gly Thr Gln Tyr Arg Ser Leu Trp Asp Pro Thr Gly Asn Leu Ser Pro
370                 375                 380

Thr Arg Arg Thr Thr Asn Tyr Asp Phe Ser Leu Tyr Thr Met Asp Pro
385                 390                 395                 400

His Glu Asn Ile Leu Leu Ser Thr Leu Glu Ile Lys Asn Glu Met Ala
                405                 410                 415

Thr Ser Glu Ala Val Met Gly Leu Gly Asp Pro Arg Ser Thr Met Leu
            420                 425                 430

Ala Tyr Asp Ala Ser Ser Ile Gln Tyr Arg Lys Ala Gly Leu Pro Arg
        435                 440                 445

His Ser Phe Gly Arg Asn Ala Leu Glu Arg His Val Ala Gln Lys Lys
450                 455                 460

Ser Arg Leu Arg Arg Arg Ala Ser Gln Leu Lys Ile Thr Ile Pro Asp
465                 470                 475                 480

Leu Thr Asp Val Asn Ala Ile Asp Arg Trp Ser Arg Ile Phe Phe Pro
                485                 490                 495

Val Val Phe Ser Phe Phe Asn Ile Val Tyr Trp Leu Tyr Tyr Val Asn
            500                 505                 510

<210> SEQ ID NO 4
<211> LENGTH: 20
<212> TYPE: PRT
<213> ORGANISM: Rattus rattus
```

```
<400> SEQUENCE: 4

Ile Leu Asp Arg Leu Leu Asp Gly Tyr Asp Asn Arg Leu Arg Pro Gly
1               5                   10                  15

Leu Gly Glu Arg
            20

<210> SEQ ID NO 5
<211> LENGTH: 15
<212> TYPE: PRT
<213> ORGANISM: Rattus rattus

<400> SEQUENCE: 5

Gly Pro Met Thr Val Leu Arg Leu Asn Asn Leu Met Ala Ser Lys
1               5                   10                  15

<210> SEQ ID NO 6
<211> LENGTH: 10
<212> TYPE: PRT
<213> ORGANISM: Rattus rattus

<400> SEQUENCE: 6

Ser Val Val Val Ala Glu Asp Gly Ser Arg
1               5                   10

<210> SEQ ID NO 7
<211> LENGTH: 18
<212> TYPE: PRT
<213> ORGANISM: Rattus rattus

<400> SEQUENCE: 7

Thr Val Phe Gly Val Thr Thr Val Leu Thr Met Thr Thr Leu Ser Ile
1               5                   10                  15

Ser Ala

<210> SEQ ID NO 8
<211> LENGTH: 17
<212> TYPE: PRT
<213> ORGANISM: Rattus rattus

<400> SEQUENCE: 8

Ser Val Val Pro Glu Lys Pro Lys Lys Val Lys Asp Pro Leu Ile Lys
1               5                   10                  15

Lys

<210> SEQ ID NO 9
<211> LENGTH: 11
<212> TYPE: PRT
<213> ORGANISM: Rattus rattus

<400> SEQUENCE: 9

Glu Pro Gln Leu Lys Ala Pro Thr Pro His Gln
1               5                   10
```